US010874479B2

(12) United States Patent
Forsell

(10) Patent No.: US 10,874,479 B2
(45) Date of Patent: *Dec. 29, 2020

(54) CHARGER FOR AN IMPLANT

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/361,652

(22) Filed: Mar. 22, 2019

(65) Prior Publication Data

US 2019/0298485 A1 Oct. 3, 2019

Related U.S. Application Data

(63) Continuation of application No. 15/431,803, filed on Feb. 14, 2017, now Pat. No. 10,238,468, which is a (Continued)

(30) Foreign Application Priority Data

Oct. 10, 2008 (SE) ........................ 0802148

(51) Int. Cl.
*A61B 5/05* (2006.01)
*A61N 1/372* (2006.01)
*A61N 1/378* (2006.01)
*A61B 17/34* (2006.01)
*A61B 90/98* (2016.01)
*A61B 90/90* (2016.01)
*A61B 34/20* (2016.01)
(Continued)

(52) U.S. Cl.
CPC .............. *A61B 90/98* (2016.02); *A61B 5/686* (2013.01); *A61B 17/3468* (2013.01); *A61B 34/20* (2016.02); *A61B 90/90* (2016.02); *A61F 2/02* (2013.01); *A61M 5/14276* (2013.01); *A61N 1/372* (2013.01); *A61N 1/3787* (2013.01); *A61N 1/37229* (2013.01); *H02J 7/0068* (2013.01); *H02J 7/025* (2013.01); *H02J 7/027* (2013.01); *H02J 50/10* (2016.02); *H02J 50/80* (2016.02); *H02J 50/90* (2016.02); *A61B 2034/2046* (2016.02); *A61B 2034/2051* (2016.02); *A61B 2560/0214* (2013.01); *A61B 2560/0219* (2013.01); *A61F 2250/0001* (2013.01); *A61M 2205/8287* (2013.01)

(58) Field of Classification Search
None
See application file for complete search history.

(56) References Cited

U.S. PATENT DOCUMENTS 6,088,619 A * 7/2000 Hein .................... A61N 1/3787
607/61
7,295,878 B1 * 11/2007 Meadows ............ A61N 1/3787
607/61

(Continued)

*Primary Examiner* — Chico A Foxx

(57) ABSTRACT

A medical device for supplying feedback information when implanted in the body of a patient is provided. The medical device is arranged to monitor or control a physiological function or defect in the body of the patient, the medical device comprises: a radio frequency identification (RFID) transmitter arranged to transmit feedback information from the implanted medical device, wherein the RFID transmitter is arranged to receive interrogating signals from an external device and in response thereto transmit feedback information.

20 Claims, 11 Drawing Sheets

Related U.S. Application Data continuation of application No. 14/809,397, filed on Jul. 27, 2015, now Pat. No. 9,566,448, which is a continuation of application No. 13/123,168, filed as application No. PCT/SE2009/051144 on Oct. 12, 2009, now Pat. No. 9,089,717.

(60) Provisional application No. 61/213,209, filed on May 18, 2009.

(51) Int. Cl.
    *H02J 50/80*     (2016.01)
    *H02J 50/90*     (2016.01)
    *H02J 50/10*     (2016.01)
    *A61B 5/00*     (2006.01)
    *A61F 2/02*     (2006.01)
    *A61M 5/142*     (2006.01)
    *H02J 7/00*     (2006.01)
    *H02J 7/02*     (2016.01)

(56) References Cited

U.S. PATENT DOCUMENTS

| | | | | |
|---|---|---|---|---|
| 7,917,226 B2* | 3/2011 | Nghiem | | A61N 1/37229 607/36 |
| 8,299,899 B2* | 10/2012 | Frysz | | G06F 19/00 340/10.1 |
| 8,339,266 B2* | 12/2012 | Nikitin | | G07G 1/009 340/10.1 |
| 9,161,693 B2* | 10/2015 | Rizwan | | A61B 5/0031 |
| 2004/0145342 A1* | 7/2004 | Lyon | | H02J 7/025 320/108 |
| 2006/0212096 A1* | 9/2006 | Stevenson | | A61B 90/98 607/60 |
| 2006/0232408 A1* | 10/2006 | Nycz | | G16H 10/65 340/572.1 |
| 2006/0246846 A1* | 11/2006 | Ginggen | | G06K 7/0008 455/69 |
| 2007/0066995 A1* | 3/2007 | Strother | | A61N 1/36007 607/2 |
| 2007/0232848 A1* | 10/2007 | Forsell | | A61F 2/0018 600/31 |
| 2007/0265677 A1* | 11/2007 | Giftakis | | A61B 5/0402 607/45 |
| 2007/0265690 A1* | 11/2007 | Lichtenstein | | A61B 5/06 607/116 |
| 2007/0279002 A1* | 12/2007 | Partovi | | H02J 7/0027 320/115 |
| 2008/0021972 A1* | 1/2008 | Huelskamp | | A61B 5/0031 709/211 |
| 2008/0030170 A1* | 2/2008 | Dacquay | | H02J 7/0004 320/137 |
| 2008/0065181 A1* | 3/2008 | Stevenson | | A61B 90/98 607/115 |
| 2008/0208010 A1* | 8/2008 | Boyden | | A61N 1/37217 600/301 |
| 2009/0221882 A1* | 9/2009 | Furman | | A61B 5/0031 600/301 |
| 2009/0270948 A1* | 10/2009 | Nghiem | | A61N 1/37229 607/60 |
| 2009/0315510 A1* | 12/2009 | Dos Santos | | H02J 7/0004 320/107 |
| 2010/0060431 A1* | 3/2010 | Stevenson | | A61B 90/98 340/10.1 |
| 2010/0194541 A1* | 8/2010 | Stevenson | | A61B 90/90 340/10.1 |
| 2010/0204756 A1* | 8/2010 | Aghassian | | A61N 1/37223 607/60 |
| 2010/0289448 A1* | 11/2010 | Jung | | H02J 7/0044 320/108 |

\* cited by examiner

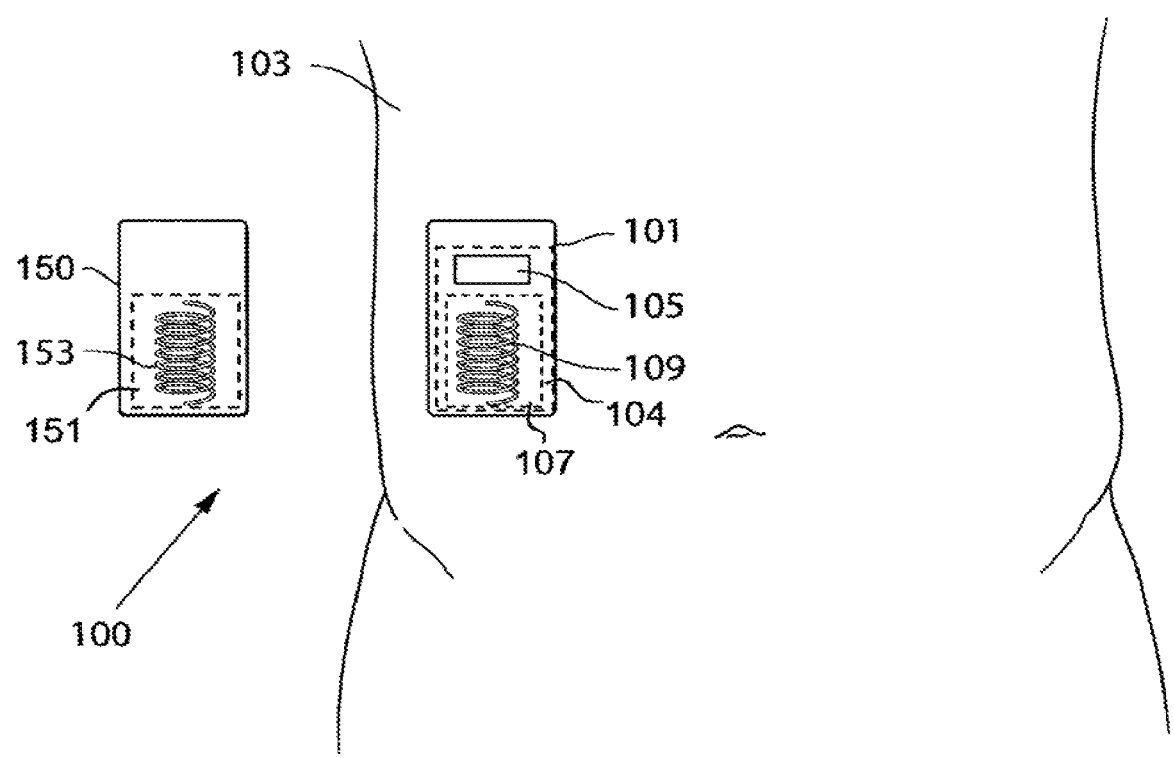

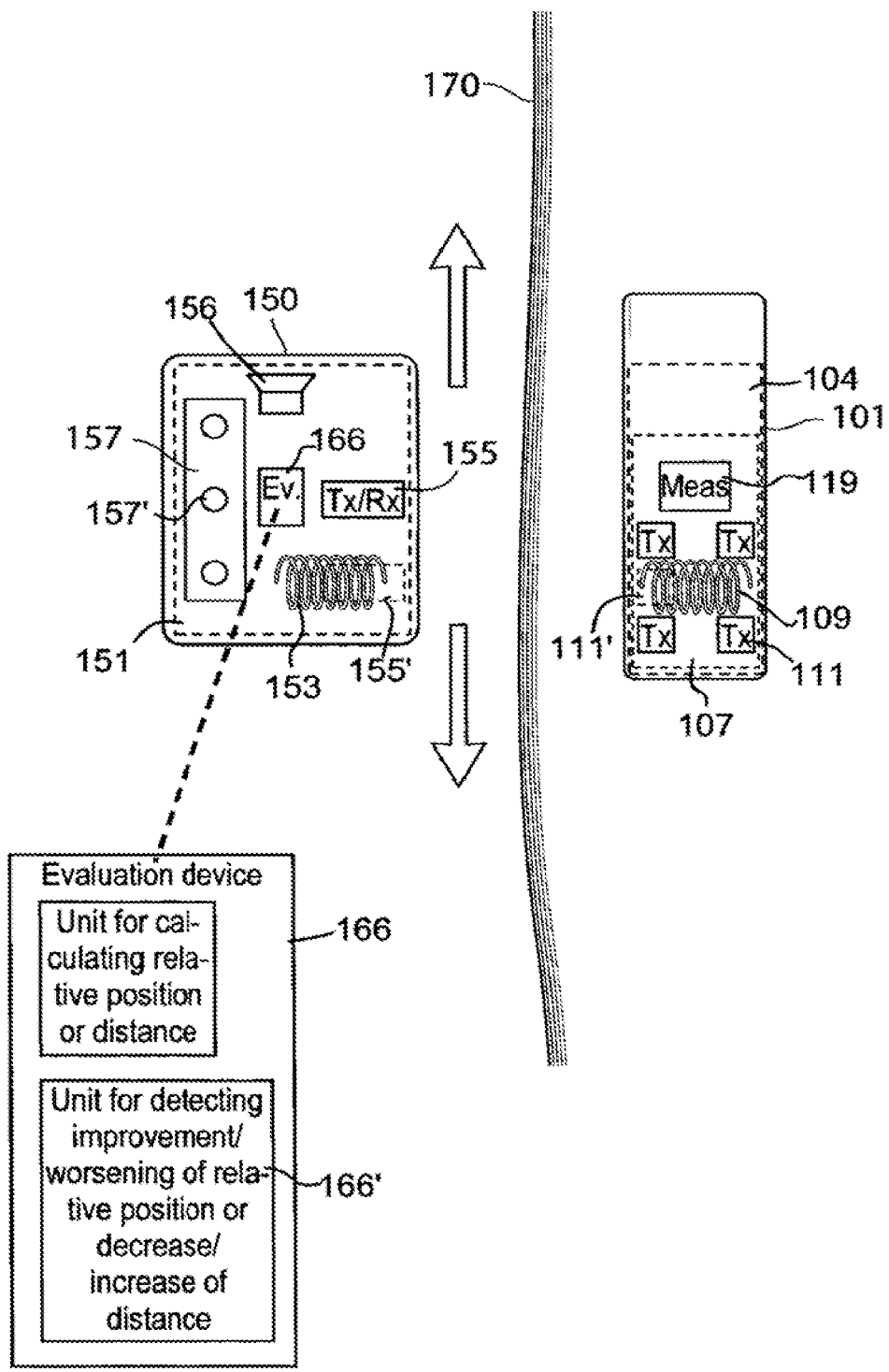

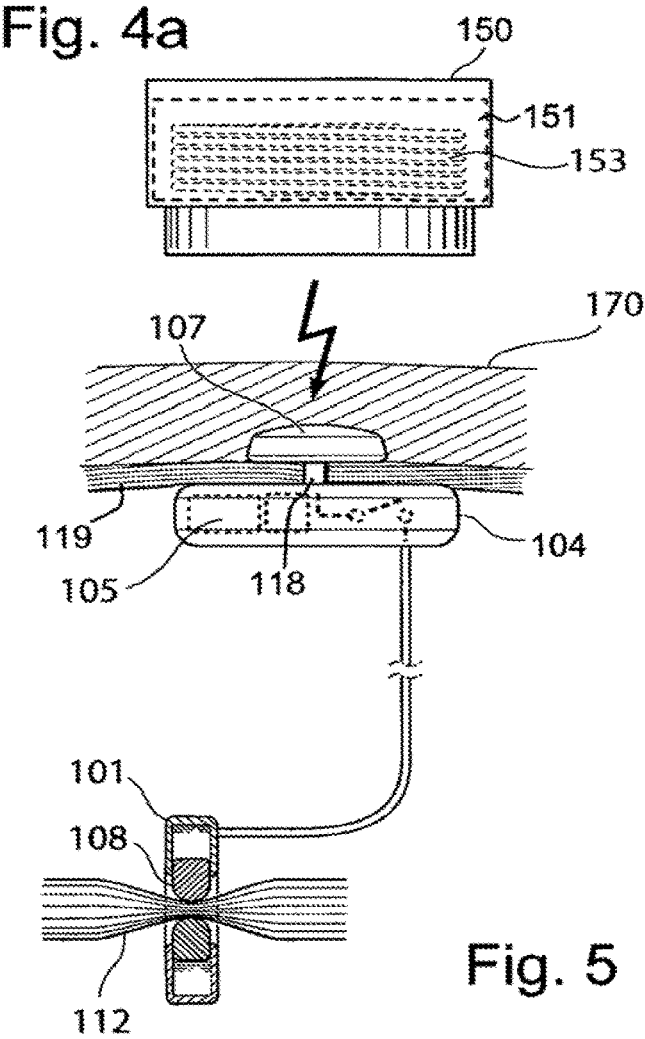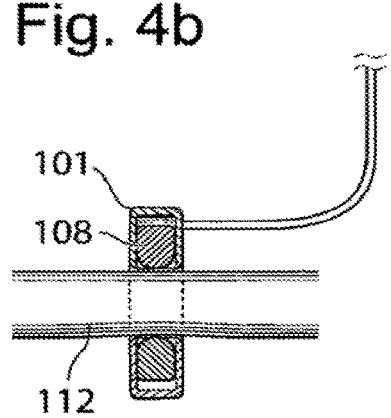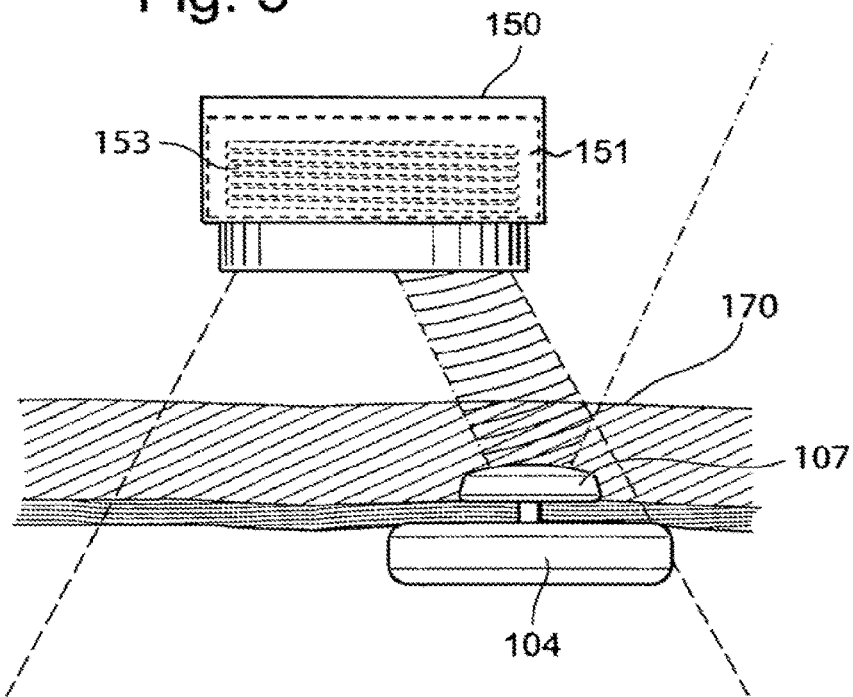

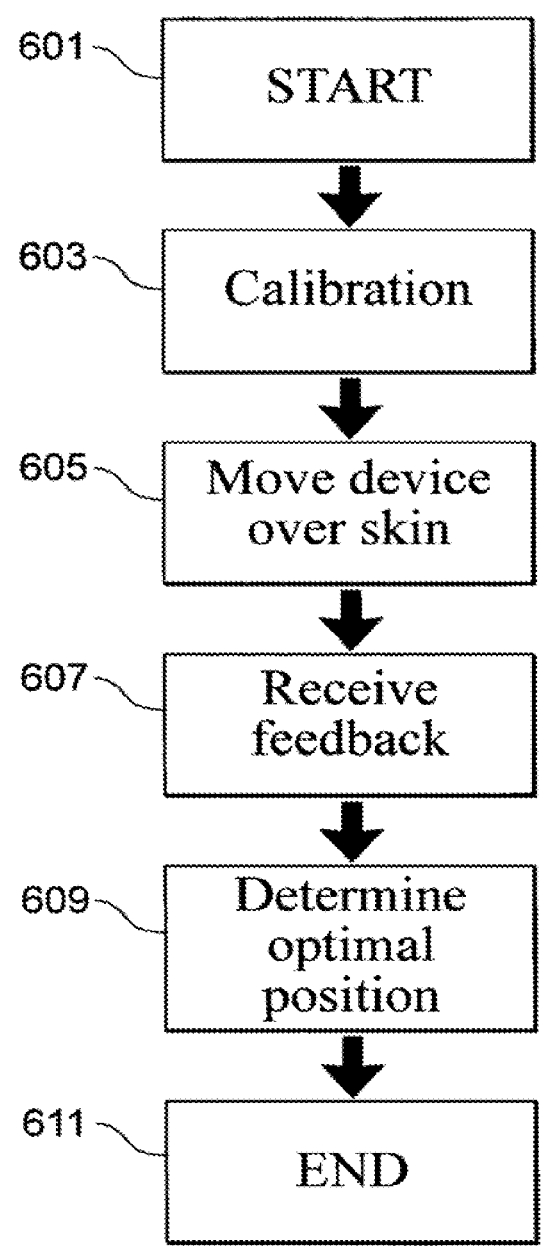

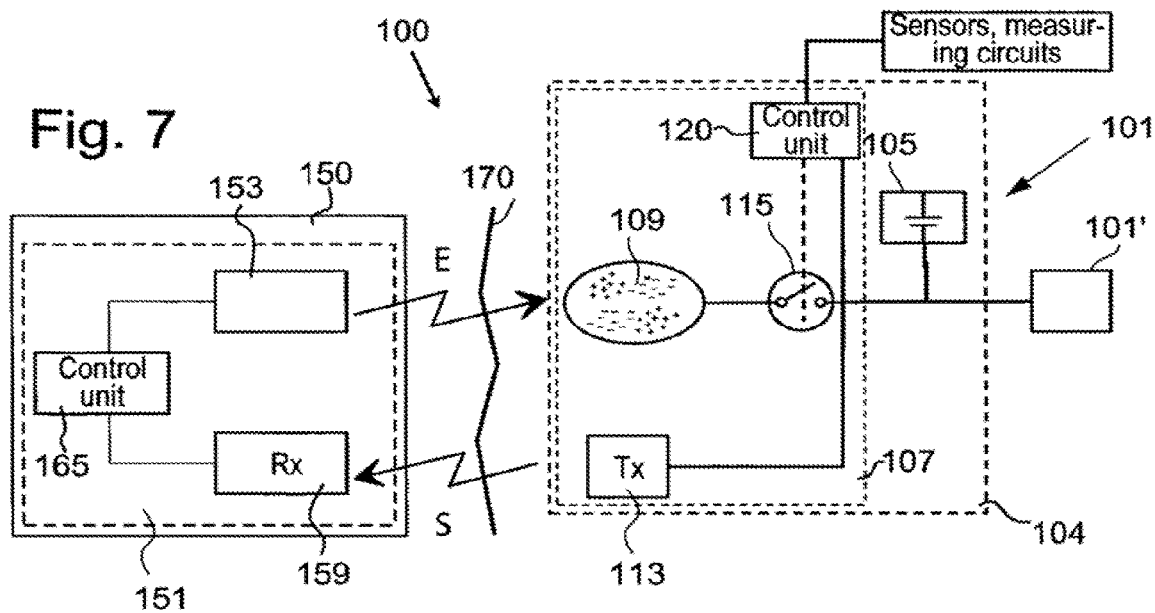
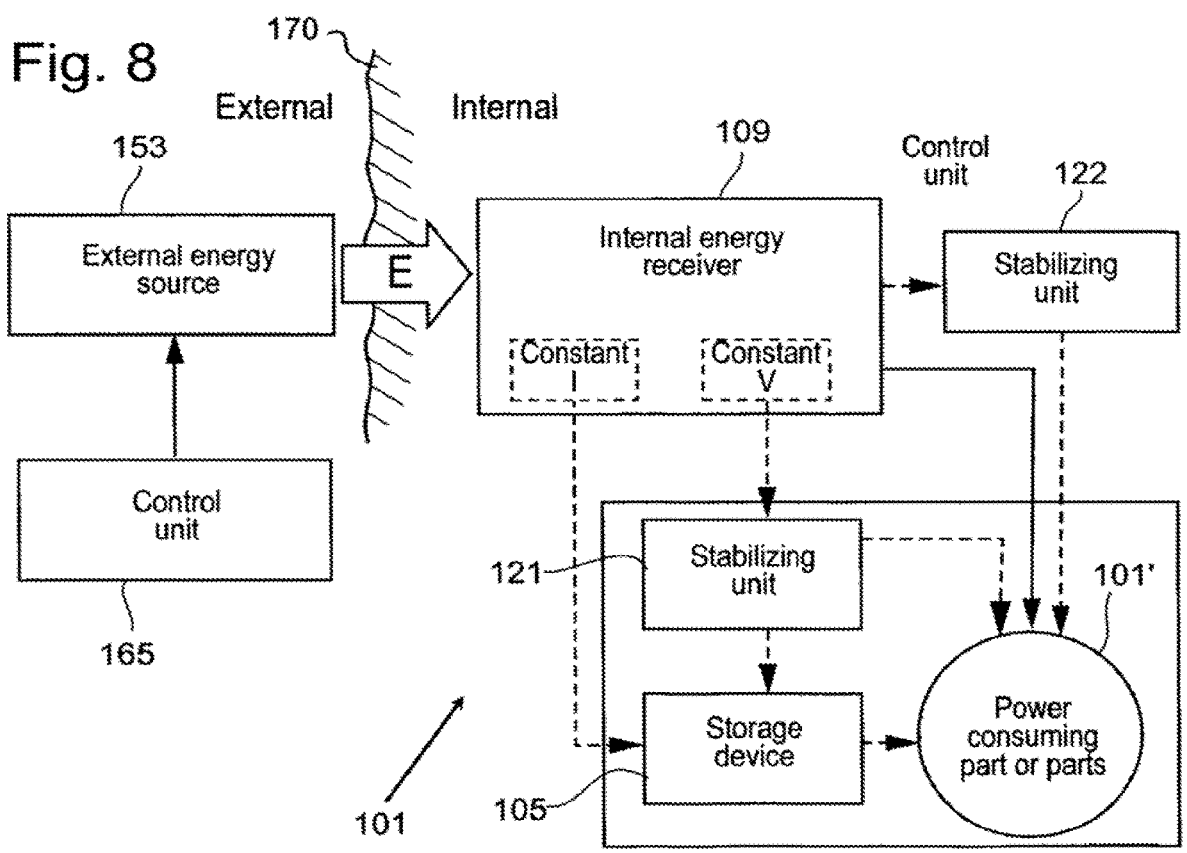

CHARGER FOR AN IMPLANT

RELATED APPLICATIONS

This application is a continuation of U.S. application Ser. No. 15/431,803, filed Feb. 14, 2017, which is a continuation of U.S. Pat. No. 9,566,448, which is the U.S. national phase of International Application No. PCT/SE2009/051144, filed Oct. 12, 2009, which designated the U.S. and claims priority to SE 0802148-7 filed Oct. 10, 2008 and the benefit of U.S. 61/213,209 filed May 18, 2009, the entire contents of each of which are hereby incorporated by reference.

TECHNICAL FIELD

The present invention relates to a method and a device for transferring energy to an implanted medical device.

BACKGROUND

Today it is becoming more and more common to implant different energy consuming devices in a human or mammal body. The implanted devices are typically provided to monitor or control a physiological function or defect in the body of a patient. Historically pacemakers have been the most common implanted medical device but other devices for controlling and monitoring other functions are being developed. For example, today such medical devices include electrical and mechanical stimulators, motors, pumps, etc., which are designed to support or stimulate various body functions. Electrical power can be supplied to such an implanted medical device from a likewise implanted battery or from an external energy transmitter that can supply any needed amount of electrical power intermittently or continuously without requiring repeated surgical operations.

In order to supply energy to an energy consuming implanted device an energy source such as an electrochemical cell or a battery is typically arranged in the implant. Electrochemical cells and batteries have a limited life time. After the electrochemical cell or battery has been emptied or discharged, it has to be re-charged or replaced. In the case of an implanted device it is for several reasons preferred to recharge an electrochemical cell or battery rather than replacing the cell or battery. One reason is the risk associated with removal of the energy source. Other reasons include that some implanted devices consume a relatively large amount of energy and would then have to have their energy sources replaced relatively often.

There is a constant need for improvements in the area of medical devices and the use thereof. Hence, there is a need for improved methods and improved devices for charging an energy source such as an electrochemical cell or a battery associated with an implanted medical device.

Methods and devices for charging a rechargeable energy source are e.g. disclosed in the published U.S. patent application 2005/0075697 and U.S. Pat. Nos. 5,702,431, 5,713,939 and 6,456,883.

SUMMARY

It is an object of the present invention to improve the performance of existing mechanisms for charging electrochemical cells, electrochemical accumulators or batteries.

It is another object of the present invention to provide an improved transfer of energy to an implanted medical device.

At least one of the above objects may be obtained by methods, devices and systems as set out in the appended claims. Thus generally, a device, also called apparatus or system, for supplying energy to an implanted medical device for implantation in a patient's body comprises an internal charger that is arranged to be implanted in the patient's body and includes a coil. The internal charger is arranged to wirelessly receive energy from an external charger also including a coil. The device may e.g. be arranged to transmit feedback information from the internal charger to the external charger, the feedback information e.g. indicating the strength of an electromagnetic field generated by the external charger.

In an embodiment a system for supplying energy to an implanted medical device or to a medical device suited for implantation in a patient's body is provided. The system can comprise an internal power supply that is arranged to be implanted in the patient's body and is associated with, such as including or connected to, a first coil. The system can further comprise an external power supply comprising a second coil arranged to charge the internal power supply by wireless transmission of energy to the internal power supply. The system may further comprise a wireless feedback system arranged to actively transmit feedback information that is related to the amount of energy that is received in a receiver associated with, such as included in or connected to, the internal power supply, the feedback information being transmitted out of the body. The feedback information can e.g. be related to the coupling factor between the first coil and the second coil. Thereby, an optimal position of the external power supply, in particular of the coil thereof, for charging the internal power supply can be found, which in turn results in a better charging of the internal power supply.

In an embodiment the system can comprise a unit for analyzing the feedback information, such as for comparing the amount of received energy to the amount of energy transmitted by the external power supply.

In an embodiment the external power supply can be arranged to be moved in relation to the internal power supply, and then it may comprise a unit for detecting an increase of the coupling factor.

In an embodiment the external power supply can be arranged to increase the amount of energy transmitted to the internal power supply until a response is detected by the external power supply, the response including feedback information relating to the value of the coupling factor.

A use of the methods, devices and systems as described herein may, at least in some cases, provide an efficient transfer of energy, and in many cases also a more efficient transfer of energy, than in existing systems, from an external power supply, also called external charger, to an internal power supply arranged to supply power to an implanted medical device.

Any feature in any of the four combinations of features in the combination embodiments described below may be used in any combination and furthermore in combination with any other feature or embodiment described or disclosed in any of the drawings, text and description of the present this application.

First Combination Embodiments Including Electrical Switching Technology

A system supplying energy to an implantable medical device when implanted in a patient's body, comprising an internal power supply arranged to be implanted in the patient's body for supplying energy to said implanted medical device, comprising a receiver comprising a first coil, an external power supply arranged to charge said internal power supply, wirelessly transmitting energy to supply the internal power supply with energy, the external power supply comprising a second coil, and a power switch to switch said first coil on and off from connection with said medical device, and a control unit arranged to control a transmission of feedback information related to the charging received in said internal power supply, received as an impedance variation in the second coil load, when said switch switches said first coil on and off.

A system, wherein the external power supply is arranged to be moved in relation to the internal power supply, resulting in an impedance variation depending on the position of said external power supply.

A system, wherein the external power supply is arranged to detect a maximum impedance variation when moved in relation to the internal power supply.

A system, further comprising an indicator arranged to indicate a better energy supply to the internal power supply in response to an increased impedance variation.

A system, wherein the external power supply is adapted to calibrate the system by increasing the amount of transferred energy to the internal power supply until a response of said impedance variation is detected.

A system, wherein the external power supply further comprises an indicator arranged to indicate a change in said impedance variation.

A system, wherein the external power supply comprises an analyzer arranged to analyze the impedance variations detected and arranged to indicate an optimal placement of said second coil in relation to said first coil based on the analyzed impedance variations.

A system, wherein the external power supply comprises a display arranged to display and/or indicate the feedback information or information derived therefrom.

A system, wherein the display comprises a number of differently colored light sources.

An internal power supply arranged to be implanted in the patient's body for supplying energy to an implanted medical device, the internal power supply comprising a receiver comprising a first coil arranged to be charged with energy wirelessly transmitted from an external power supply, wherein the internal power supply is associated with a power switch to switch said first coil on and off from connection with said medical device, and further comprising a control unit arranged to control transmission of a feedback information related to the charging received in said internal power supply, received as an impedance variation in the coil load, when said switch switches said first coil on and off.

An external power supply arranged to charge an internal power supply comprising a first coil and arranged to supply an implanted medical device with energy, the external power supply arranged to wirelessly transmit energy to supply the internal power supply with energy, the external power supply comprising a second coil, the external power supply further comprising a receiver for receiving feedback information related to the charging received in said internal power supply as an impedance variation in the first coil load, when the connection between the first coil and the implanted medical device is switched on and off.

An external power supply, wherein the external power supply is arranged to be moved in relation to the internal power supply, resulting in an impedance variation depending on the position of said external power supply.

An external power supply, further comprising an indicator arranged to indicate a better energy supply to the internal power supply in response to an increased impedance variation.

A external power supply, wherein the external power supply is arranged to increase the amount of transferred energy to the internal power supply until a response of said impedance variation is detected.

An external power supply, wherein the external power supply further comprises an indicator arranged to indicate a change in impedance variation.

An external power supply, wherein the external power supply comprises an analyzer arranged to analyze the impedance variations detected and arranged to indicate an optimal placement of said second coil in relation to said first coil based on the analyzed impedance variations.

An external power supply, wherein the external power supply comprises a display arranged to display the feedback information or information derived therefrom.

An external power supply, wherein the display comprises a number of differently colored light sources.

A method for supplying energy to an implanted medical device comprising an internal power supply arranged to be implanted in a patient's body, the internal power supply comprising a receiver comprising a first coil and a power switch, the device further comprising an external power supply comprising a second coil, the method comprising the steps of:

charging said internal power supply using wirelessly transmission of energy to the internal power supply, switching said first coil on and off from connection with said medical device, transmitting feedback information related to the charging received in said internal power supply, and receiving said feedback information as an impedance variation in the second coil load, in response to switching said first coil on and off.

A method, further comprising the step of moving the external power supply in relation to the internal power supply.

A method, further comprising the step of increasing the amount of transferred energy to the internal power supply until a response of said impedance variation is detected.

A method, further comprising the step of indicating a positive or negative change in the impedance variation.

A method, further comprising the step of indicating an optimal placement of said second coil in relation to said first coil in response to a maximal impedance variation.

A method, further comprising the steps of:

analyzing the impedance variation, and optimizing the placement for maximum impedance variation of said second coil in relation to said first coil based on the analyzed impedance variations.

A method, further comprising the step of generating a signal indicative of the impedance variation.

A method, further comprising the step of indicating and/or displaying the feedback information or information derived therefrom.

A method, wherein the displayed feedback information is displayed by a number of differently colored light sources.

A method of using the features above, comprising the steps of:

creating an opening in the skin of a mammal patient, dissecting an one area of the patient, placing the internal power supply device within said area, charging said internal power supply postoperatively and non-invasively by wirelessly transmitting energy from an external power supply, said internal power supply further comprising a switch connecting said internal power supply with said medical implant, switching said switch on and off, wirelessly receiving feedback information from the internal power supply out of the patient's body as impedance variation, when said switch switching on and off.

A method, comprising the step of moving said external power supply, maximizing said impedance variation, and optimizing the placement of said external power supply in relation to said internal power supply.

A method, wherein the step of creating an opening in the skin comprises:

inserting a tube or needle into the patient's body, filling the body through the tube or needle with a gas and thereby expanding a cavity within the patient's body, inserting at least two laparoscopic trocars into said cavity, inserting at least one camera through at least one laparoscopic trocar, inserting at least one dissecting tool through at least one laparoscopic trocar.

Second Combination Embodiments Including Massive Electromagnetic Feedback Technology A system for supplying energy to an implantable medical device when implanted in a patient's body, comprising an internal power supply arranged to be implanted in the patient's body, comprising a receiver comprising a first coil, an external charger arranged to wirelessly transmit energy to charge said internal power supply with energy, the external power supply comprising a second coil, and a receiver in the external power supply for receiving passively transmitted feedback information from the first coil generated in response to a power pulse or burst transmitted by the external power supply.

A system, wherein the receiver is arranged to determine the strength of said electromagnetic field generated by the first coil.

A system, wherein the external power supply is arranged to be moved in relation to the internal power supply, and wherein the external power supply comprises an indicator arranged to indicate a response to said energy pulse or burst depending on the position of said external power supply.

A system, wherein the external charger is arranged to display the determined strength of said electromagnetic field when the external power supply is moved in relation to said internal power supply.

A system, wherein the external power supply is arranged to increase the amount of transferred energy to the internal power supply until a response of said bursts/pulses is detected.

A system, wherein the external power supply comprises an analyzer arranged to display the strength or magnitude of the detected electromagnetic field.

A system, wherein the external power supply further comprises a sensor arranged to generate a signal indicative of a magnetic field returning from the first coil.

A system, wherein the external power supply comprises a display arranged to display the feedback information or information derived therefrom.

A system, wherein the display comprises a number of differently colored light sources.

A method of supplying energy to an implanted medical device, the device comprising an internal power supply implanted in the patient's body comprising a first coil, the device further comprising an external charger having a second coil, the method comprising the steps of:

wirelessly transmitting energy from the external charger to the internal power supply charging said internal power supply with energy, and receiving in the external power supply passively transmitted feedback information from the first coil generated in response to a power pulse or burst transmitted by the external power supply.

A method, further comprising the step of determining in the external power supply the strength of said electromagnetic field generated by the first coil.

A method, further comprising the steps of:

moving the external power supply in relation to the internal power supply, and indicating a response to said energy pulse or burst.

A method, further comprising the step of indicating the position where the response is maximized as optimal position of said external power supply.

A method, further comprising the step of increasing the amount of transferred energy to the internal power supply until a response of said bursts/pulses is detected.

A method, further comprising the step of indicating or displaying the strength or magnitude of the detected electromagnetic field.

A method, further comprising the step of generating a signal indicative of a returning magnetic field from the first coil.

A method, further comprising the step of indicating or displaying the feedback information or information derived therefrom.

A method, wherein the displayed feedback information is displayed by a number of differently colored light sources.

Third Combination Embodiments Including Coupling Factor Technology

A system for supplying energy to an implantable medical device when implanted in a patient's body, the system comprising:

an internal power supply arranged to be implanted in the patient's body, comprising a receiver comprising a first coil, an external power supply comprising a second coil arranged to charge said internal power supply using wireless transmission of energy to the internal power supply, and a wireless feedback system arranged to actively transmit feedback information related to the received amount of energy in the receiver, out of the body, wherein the feedback information is related to the electromagnetic coupling such as the coupling factor between the first and second coils.

A system further comprising a unit for comparing the feedback information to the amount of energy transmitted by the external power supply.

A system, wherein the external power supply is arranged to be moved in relation to the internal power supply, and further comprising a unit for detecting an increase or decrease in the electromagnetic coupling such as said coupling factor.

A system, wherein the external power supply is arranged to increase the amount of transferred energy to the internal power supply until a response of said coupling factor is detected.

A system, wherein the external power supply further comprises an indicator arranged to indicate a positive or negative change in the electromagnetic coupling such as the coupling factor.

A system, wherein the external power supply further comprises an indicator arranged to indicate an optimal placement of said second coil in relation to said first coil to optimize the electromagnetic coupling such as said coupling factor.

A system, wherein the external power supply is freely movable to an optimal placement position of said second coil in relation to said first coil.

A system, wherein the external power supply further comprises an analyzer arranged to analyze the amount of energy being transmitted and arranged to receive feedback information related to the amount of energy received in the receiver, and further arranged to determine a value of the electromagnetic coupling such as the coupling factor by comparing the amount of transmitted energy and the feedback information related to the amount of received information.

A system, wherein the external power supply further comprises a sensor arranged to generate a signal indicative of the coupling factor.

A system, wherein the external power supply comprises a display arranged to display the feedback information or information derived therefrom.

A system, wherein the display comprises a number of differently colored light sources.

An internal power supply arranged to be implanted in a patient's body, comprising a receiver comprising a coil, wherein the internal power supply is arranged to be charged via using wireless transmission of energy to the internal power supply, and further comprising a wireless feedback system arranged to actively transmit feedback information related to the received amount of energy in the receiver, out of the body, wherein the feedback information is related to the amount of energy being received.

An external power supply comprising a second coil arranged to charge an implantable power supply comprising a first coil using wireless transmission of energy to the internal power supply, the external power supply further comprising a receiver for receiving actively transmitted feedback information related to the received amount of energy in the implantable power supply, wherein the feedback information is related to the coupling factor between the first and second coils.

An external power supply, wherein the power supply further comprises a unit for comparing the feedback information to the amount of energy transmitted by the external power supply.

An external power supply, wherein the external power supply is arranged to be moved in relation to the internal power supply, and further comprising a unit for detecting an increase in said coupling factor, to allow to maximize said increase.

An external power supply, wherein the external power supply is arranged to increase the amount of transferred energy to the internal power supply until a response of said coupling factor is detected.

An external power supply, wherein the external power supply further comprises an indicator arranged to indicate a positive or negative change in the coupling factor.

An external power supply, wherein the external power supply further comprises an indicator arranged to indicate an optimal placement of said second coil in relation to said first coil to optimize said coupling factor.

An external power supply, wherein the external power supply further comprises an analyzer arranged to analyze the amount of energy being transmitted and arranged to receive feedback information related to the amount of energy received in the receiver, and further arranged to determine the coupling factor by comparing the amount of transmitted energy and the feedback information related to the amount of received energy.

An external power supply, wherein the external power supply further comprises a sensor arranged to generate a signal indicative of the coupling factor.

An external power supply, wherein the external power supply comprises a display arranged to display the feedback information.

An external power supply, wherein the display comprises a number of differently colored light sources.

A method of energy transfer to an implanted medical device in a patient's body, the device comprising an internal power supply comprising a receiver comprising a first coil from an external power supply comprising a second coil, the method comprising the steps of:
charging said internal power supply using wireless transmission of energy to the internal power supply, and
wirelessly transmitting feedback information related to the received amount of energy in the receiver, out of the body, wherein the feedback information is related to the electromagnetic coupling such as the coupling factor between the first and second coils.

A method, wherein the method further comprises the step of comparing the feedback information to the amount of energy transmitted by the external power supply.

A method further comprising the step of:
moving the external power supply in relation to the internal power supply, and
detecting an increase in said coupling factor, in response to movement of said external power supply to maximize said increase.

A method, further comprising the step of increasing the amount of transferred energy to the internal power supply until a response of said coupling factor is detected.

A method, further comprising the step of indicating a positive or negative change in the coupling factor.

A method, further comprising the step of indicating an optimal placement of said second coil in relation to said first coil to optimize said coupling factor.

A method, further comprising the steps of:
analyzing the amount of energy being transmitted,
receiving feedback information related to the amount of energy received in the receiver, and
determining a value of the electromagnetic coupling such as the coupling factor by evaluating/comparing the amount of transmitted energy and the feedback information related to the amount of received energy.

A method, further comprising the step of generating a signal indicative of the coupling factor.

A method, further comprising the step of indicating displaying the feedback information or information derived therefrom.

A method, wherein the displayed information is displayed by a number of differently colored light sources.

A method of operating a device apparatus comprising the steps of:
creating an opening in the skin of a mammal patient,
dissecting an area of the patient,
placing the internal power supply device within said area,
charging said internal power supply postoperatively and non-invasively by
wirelessly transmitting energy from an external power supply,
wirelessly transmitting feedback information from the internal power supply out of the patient's body, said feedback related to the amount of received energy, and
comparing the received energy with the transmitted energy in the external power supply.

A method, wherein the step of comparing the energy includes comparing the coupling factor of the coils.

A method, comprising the step of moving said external power supply for maximizing said coupling factor.

A method, wherein the step of creating an opening in the skin comprises the steps of:
inserting a tube or needle into the patient's body,
filling the body through the tube or needle with a gas and thereby expanding a cavity within the patient's body,
inserting at least two laparoscopic trocars into said cavity,
inserting at least one camera through at least one laparoscopic trocar, and
inserting at least one dissecting tool through at least one laparoscopic trocar.

A system for supplying energy to an implanted medical device for implantation in a patient's body, comprising
an internal charger arranged to be implanted in the patient's body, the internal charger comprising a first coil,
an external charger arranged to wirelessly transmit energy to supply the internal charger with energy, the external charger comprising a second coil, and
a wireless feedback system arranged to transmit feedback information from the internal charger to the external charger, wherein the feedback information is related to the strength of an electromagnetic field generated by the external charger.

Fourth Combination Embodiments Including Passive RFID Technology

A system for supplying energy to an implantable medical device when implanted in a patient's body, comprising
an internal charger arranged to be implanted in the patient's body comprising a first coil,
an external charger arranged to wirelessly transmit energy to supply the internal charger with energy, the external charger comprising a second coil, and
a wireless feedback system arranged to transmit feedback information from the internal charger to the external charger, wherein the feedback information is based on information from at least one Radio Frequency Identification, RFID, transmitter.

A system, wherein the feedback information is related to the strength of an electromagnetic field generated by the external charger.

A system, wherein the RFID transmitter is arranged to change identification in response to the received electromagnetic field.

A system, wherein the wireless feedback system comprises more than one RFID transmitter or receiver.

A system, further comprising a triangulation module for determining the position of the internal charger based on triangulation of the RFID transmitter/s/.

A system, wherein the external charger comprises a display arranged to display the feedback information or information derived therefrom.

A system, wherein the display comprises a number of differently colored light sources.

A method of supplying, to an implantable medical device when implanted in a patient's body, comprising an internal power supply arranged to be implanted in the patient's body comprising a first coil, energy from an external power supply comprising a second coil, the method comprising the steps of:
wirelessly transmitting energy to supply the internal power supply with energy, and
receiving feedback information from the internal power supply by the external power supply, wherein the feedback information is based on information from at least one Radio Frequency Identification, RFID, transmitter.

A method, wherein the feedback information is related to the strength of an electromagnetic field generated by the external power supply.

A method, wherein the RFID transmitter identification is set in response to the received electromagnetic field.

A method, wherein the wirelessly transmitted feedback information is transmitted and/or received using more than one RFID transmitter and/or more than one RFID receiver.

A method, further comprising the step of determining the position of the internal power supply based on triangulation of the RFID transmitter/s/.

A method, further comprising the step of indicating or displaying the feedback information or information derived therefrom.

A method, wherein the feedback information is displayed using a number of differently colored light sources.

A method of using a system or device, comprising the steps of:
creating an opening in the skin of a patient,
dissecting an area of the patient,
placing the internal power supply device within said area,
charging said internal power supply postoperatively and non-invasively by
wirelessly transmitting energy from an external power supply, said internal power supply further comprising a RFID identification,
wirelessly receiving feedback information from the internal power supply out of the patient's body as said RFID identification.

A method, further comprising the step of moving said external power supply, for maximizing said RFID identification, and optimizing the placement of said external power supply in relation to said internal power supply based on a maximized RFID identification.

A method, wherein the step of creating an opening in the skin comprises:
inserting a tube or needle into the patient's body,
filling the body through the tube or needle with a gas and thereby expanding a cavity within the patient's body,
inserting at least two laparoscopic trocars into said cavity,
inserting at least one camera through at least one laparoscopic trocar, and
inserting at least one dissecting tool through at least one laparoscopic trocar.

Additional objects and advantages of the invention will be set forth in the description which follows, and in part will be obvious from the description, or may be learned by practice of the invention. The objects and advantages of the invention may be realized and obtained by means of the methods, processes, instrumentalities and combinations particularly pointed out in the appended claims.

BRIEF DESCRIPTION OF THE DRAWINGS

While the novel features of the invention are set forth with particularly in the appended claims, a complete understanding of the invention, both as to organization and content, and of the above and other features thereof may be gained from and the invention will be better appreciated from a consideration of the following detailed description of non-limiting embodiments presented hereinbelow with reference to the accompanying drawings, in which:

FIG. 1 is a general schematic view of an implanted device charger arrangement,

FIGS. 2a and 2b are schematic views of charger arrangements in accordance with first embodiments, FIGS. 4a and 4b are schematic views of a chargeable medical device, FIG. 5 is a schematic view illustrating the operation of a charger system, FIG. 6 is a flowchart illustrating the operation of a charger system, FIG. 7 is a schematic view of an implanted chargeable medical device, FIG. 8 is a schematic view of an implantable medical device.

DETAILED DESCRIPTION

Figure 2B:
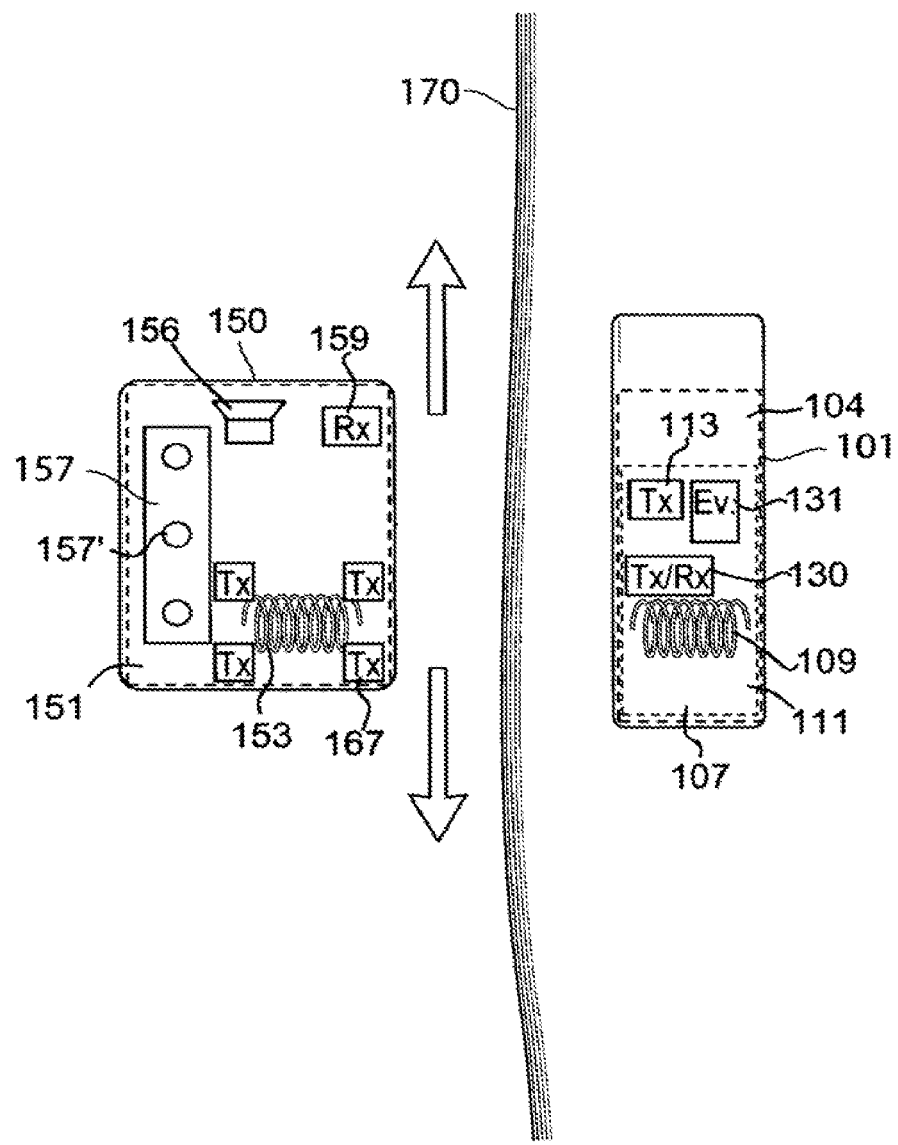

In FIG. 1 an arrangement 100 for charging an implanted medical device 101 is shown. The implantable medical device 101 implanted in a patient 103 includes or is connected to an internal power supply 104 containing or connected to an internal energy source. The internal energy source can for example comprise an energy accumulator such as an electrochemical cell or battery 105 or a capacitor, the energy accumulator generally also called "battery" herein. The energy source is rechargeable and can be charged by the internal power supply 104 such as by energy received from an internal charger 107 included in or connected to the internal power supply. The internal charger can typically include or be connected to a first coil 109 that is arranged to be influenced by an electromagnetic field created by an external power supply 150 containing or connected to an external charger 151. The external charger device can typically comprise or be connected to a second coil 153 that is arranged to generate an electromagnetic field for creating an electric current in the first coil 109, thereby allowing the charging of the battery 105. The first coil can be called an energy receiver and the second coil an energy transmitter.

In order provide an efficient and secure transfer of energy through the skin of the patient 103 it may be important for a user of the external charger 151 to gain knowledge of the position of the implanted medical device 101 so that the electromagnetic field generated by the second coil 153 can be correctly controlled. Hence, an electromagnetic field for creating an electric current used for charging the battery 105 of the internal power supply 104 should be sufficiently strong in order to provide a short charging time of the battery. On the other hand the electromagnetic field should not be too strong since a strong electromagnetic field could endanger the internal charger 107 or cause other problems, such as causing problems to tissues of the patient's body 103.

In order to gain knowledge of the position of the implanted medical device 101 and in particular of the first coil 109 feedback information can be used.

FIGS. 2*a* and 2*b* are schematics of two embodiments. In these embodiment a plurality of Radio Frequency Identification (RFID) transmitters are provided in the internal charger 107 and/or in the external charger 151 for facilitating the localizing of the implanted medical device and in particular localizing the first coil 109 thereof, i.e. for finding the position thereof in relation to the external, second coil 153.

Generally RFID is a method of remotely storing and retrieving identification data. For RFID devices called RFID tags are often used. An RFID tag is a relatively small object that can easily be attached to or incorporated into any product. An RFID tag contains an antenna to allow it to receive and respond to radio-frequency queries from an RFID transceiver. RFID tags can be either active or passive. RFID tags can be passive and then they have no own power supply. The small electrical current induced in the antenna by the incoming radio-frequency wave provides power for the tag to send a response containing an identification of the tag such as an ID number. Active RFID tags have own power sources and may have longer ranges and larger memories than passive tags as well as the capability of storing additional information sent by the transceiver. For example, in the case where passive RFID devices are used, an optimal position of the external charger in relation to the internal charger can be found also in cases where the implanted device has totally been emptied of energy and the position of the implanted device and in particular of the internal charger is not known to the user or operator such as when a patient receives care in a foreign hospital.

In the embodiment of FIG. 2*a* the RFID transmitters 111 are located in the internal charger 107, in a symmetrical position around the internal coil 109. For example four RFID transmitters can be arranged which then can arranged in the corners of a square. The external charger 151 is provided with a transceiver 155, also called interrogator or RFID receiver, for issuing interrogating signals and receiving transmitted RFID signals in response thereto. The transceiver 155 should be located centrally in relation to the external coil 151 such as just in front of it or behind seen in a direction centrally through the external coil and perpendicularly to the surface of the external charger that is facing the skin of the patient and arranged to be in contact therewith, a suitable position indicated by the dashed lines at 155' in FIG. 2*a*.

Different methods may be used for determining or estimating the position of the external coil—strictly the position of the transceiver—in relation to the internal coil 109—strictly the position of the RFID transmitters 111. In one method the RFID transmitters are arranged to respond selectively so that there is a specific interrogation signal for each transmitter. The transceiver 155 can then measure the length of the time period between interrogation signal and response. The measured lengths can be compared in an evaluation unit 166 which compares the lengths to each other and generates a signal according to the result of the comparing. In another method the RFID transmitters 111 are arranged to respond to the same interrogation signal but the transceiver 155 contains a plurality of antenna elements and the times when the signals from the RFID transmitters containing the identifications thereof are measured. The measured times are evaluated in the evaluation unit 166 to find the geometrical direction from the transceiver to the respective RFID transmitter. The directions are evaluated in relation to each other to find the relative position of the transceiver. This can be called a triangulation method.

In another embodiment the RFID signature is set in response to the magnitude of the received electromagnetic field as measured by a measurement unit 119 in the internal charger 107. A value of the magnitude can e.g. be obtained by measuring the voltage induced in the internal coil 109. Alternatively, the strength of the RF interrogating electromagnetic field can be sensed by the receiving RFID transmitter. Then, only one RFID transmitter 111 is required which should be placed symmetrically or centrally in relation to the internal coil 109. A suitable position of the single RFID transmitter is indicated by the dashed lines at 111' in FIG. 2*a*. In the same way as in other embodiments the user can sweep over or scan the skin 170 of the patient with a low charging power. The internal measurement unit 119 then determines, when receiving an interrogation signal from the transceiver 155, the strength of the received electromagnetic field and provides the determined value of the strength to the RFID transmitter. The RFID transmitter 111 sets its identification accordingly and thereafter transmits it to the transceiver.

In another simple embodiment also only one RFID transmitter 111 is used which when interrogated responds with a signal holding its information. The transceiver 155 can then measure the length of the time period between interrogation signal and response to find a value of the distance between external charger and the internal charger.

Hence, the position of the first coil 109 of the implanted medical device 101 in relation to the external coil 153 or the distance therebetween can be calculated and information thereof can be fed back to the user. Information can also be fed back when the external charger 151 and in particular the second coil 153 is placed in an optimal position for transmitting energy to the internal charger.

The evaluation unit 166 thus generates a signal holding information about the current relative position of the external charger or the distance, respectively. This signal can be provided a display 157. In one embodiment the display is arranged to display the position relative to an optimal position. For example the display may comprise a number of light emitting diodes (LEDs) 157T of different colors indicating the current position or distance. For example a red light emitting diode may be lit when the external charger 151 is far off from an optimal position. When the external charger is moved closer to an optimal position, a yellow diode can be lit and when the external charger is in or close to an optimal position a green diode can be lit. Alternatively, the display can include single light source emitting light pulses with a repetition frequency that indicates the measured relative position, a higher repetition frequency indicating that the external coil 153 is closer to the optimal position or vice versa.

Furthermore, in order to provide such signals the successively determined values of the relative position or the distance between the external and internal chargers, obtained when the external charger 151 is being moved, can be further evaluated in a detecting unit 166' determining whether the relative position or the distance is currently being improved, i.e. more close, or is currently decreasing, respectively, or not, by comparing the latest determined relative position or value of the distance to the next latest determined position or value. This may be necessary in order to generate a signal provided to an indicator such as the display 157 or a loudspeaker or sound generating unit as will be described below.

Such a signal can thus indicate an improved or worsened relative position of the external charger 151 or and the at least one RFID transmitter 111 or a positive or negative change of the distance between the external charger and the at least one RFID transmitter. In the case where the at least one RFID transmitter is located in the external charger, the signal can indicate an improved or worsened relative position of the internal charger 107 or and the at least one RFID transmitter 167 or a positive or negative change of the distance between the external charger and the at least one RFID transmitter.

As a supplement or an alternative to the display 157 the external charger 151 can be provided with a unit 156 also receiving the signal holding information about the current relative position or distance and providing an audible signal, the characteristics of which is changed according to the determined relative position of or distance between the external charger and the internal charger 107. Thus, the audio unit can e.g. emit a sound signal having a low strength or a low pitch when the determined value of the relative position indicates a large distance and having a higher strength or a high pitch, respectively, when the determined value of the relative position indicates that external charger is closer to the internal charger value, the strength or pitch being set according to the determined distance, or vice versa. In an alternative the sound is emitted as pulses, the repetition frequency of which is changed depending on the value of the relative position.

The user moves the external charger 151 to find, using the output therefrom such as the visible indication on the display or the sound signal, the position in which optimal charging conditions exist. Thereupon, the use can tune the charging, i.e. the level of transfer or transmission of energy, to an optimal power level.

During the procedure of finding an optimal position the transceiver 155 can at regularly repeated times issue interrogation signals to the RFID transmitters/transmitter 111.

In the case illustrated in FIG. 2b the RFID transmitter or transmitters 167 are placed in the external charger 151 and the RFID receiver 130 in the internal charger 107. An evaluation unit 131 is arranged in the internal charger for evaluating the feedback information received from the RFID transmitter/transmitters. The result of the evaluation can be transmitted to the external charger using a transmitter 113 in the internal charger and a receiver 159 in the external charger.

In another embodiment the RFID transmitter/s/are replaced with RFID receiver/s/and the RFID receiver is replaced with an RFID transmitter, this case not shown in the drawings. Thus, e.g. the four RFID transmitters 111 of FIG. 2a could be replaced with RFID receivers and the RFID receiver with an RFID transmitter. Time periods between challenging or interrogating signals and responses or angles of the response signals can be measured as described above and evaluated by a unit in the internal charger 107. In an alternative, the four RFID transmitters of FIG. 2b could be replaced with four RFID receivers and the single RFID receiver 130 with an RFID transmitter. The evaluation unit is in the latter case placed in the external charger.

Figure 3A:
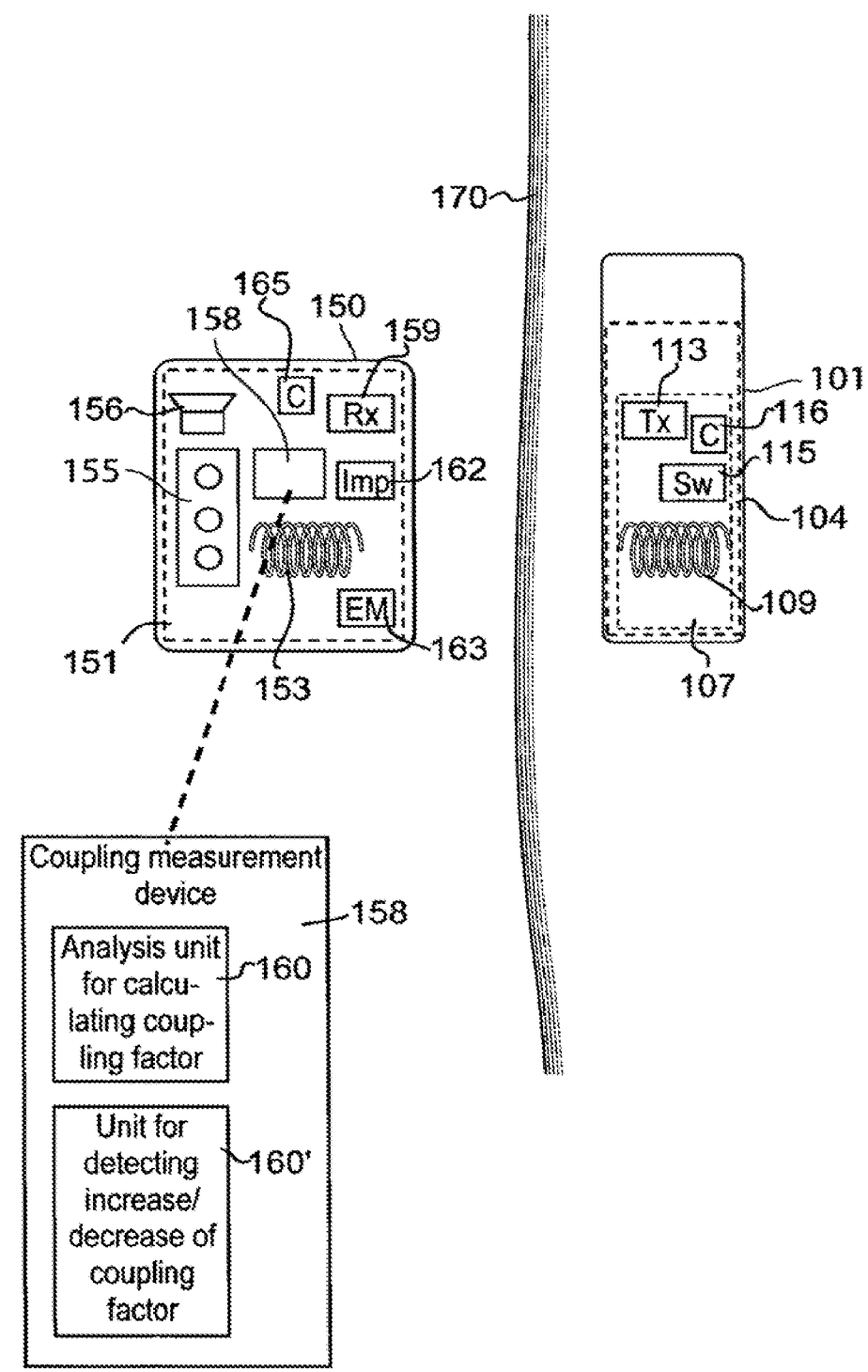
FIGS. 3a and 3b are schematic views of a charger arrangement in accordance with a second embodiment.
Figure 3B:
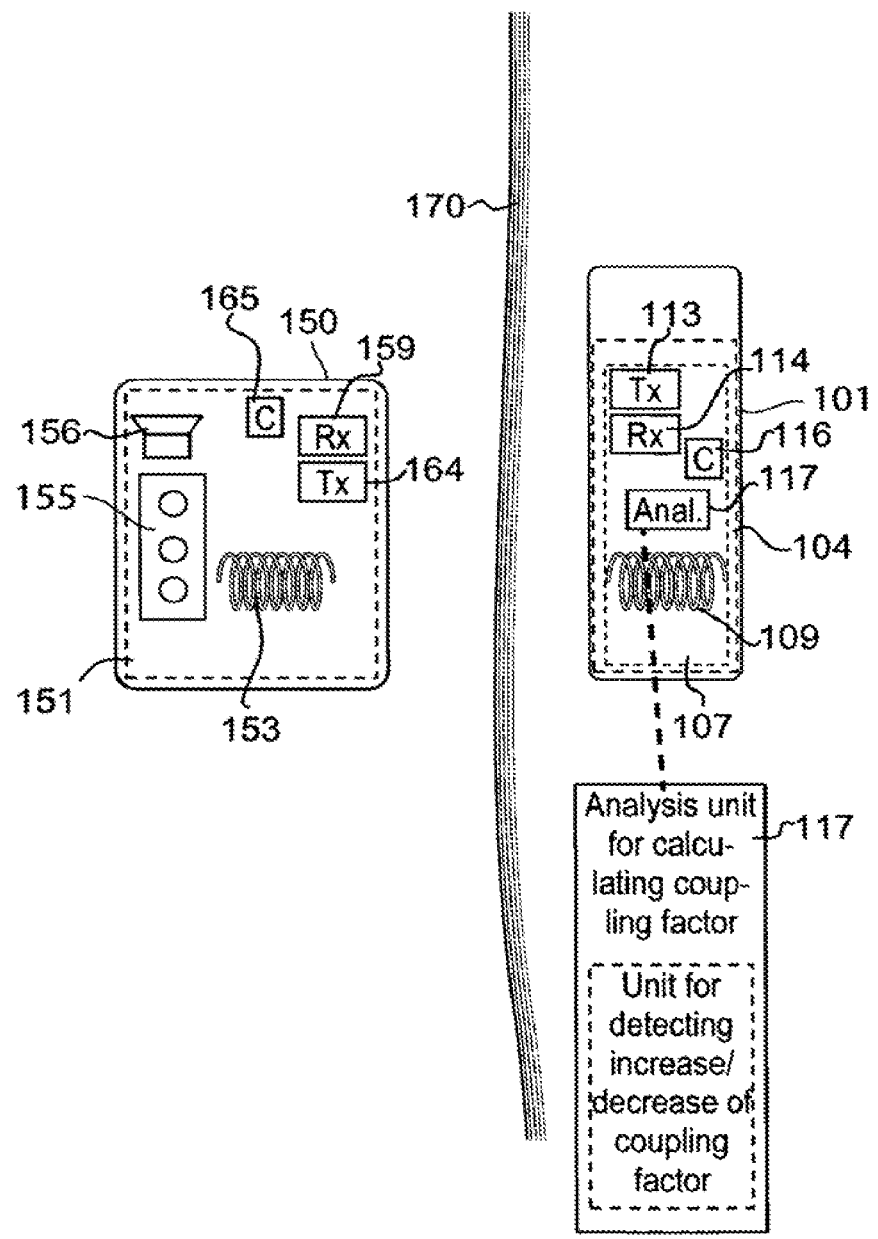

FIGS. 3a and 3b are schematics of another embodiments. In these embodiments the external charger 151 and/or the internal charger 107 is/are arranged to measure the mutual coupling between the external charger and internal charger using a coupling measurement device. In the case shown in FIG. 3a the coupling measurement device 158 is placed in the external charger. A user can sweep over or scan the skin of the patient with the external charger 151 using a low charging power to find, based on feedback from the coupling measurement device, an optimal position, the optimal position being the position in which the coupling measurement device indicates the highest coupling factor. After having found the optimal position providing optimum charging conditions, the user can tune the charging to an optimum power level of the transmitted field for charging the battery 109 of the implanted medical device 101.

The coupling measurement device 158 is in one embodiment arranged to analyze, such as in an analysis unit 160, the amount of energy being transmitted from the external charger 151 and also to receive feedback information about the amount of energy actually received by the internal charger 107. By calculating the ratio between the transmitted amount of energy and the received amount of energy a coupling factor can be determined. Furthermore, the successively determined values of the coupling factor, obtained when the external charger 151 is being moved, can be further evaluated in a detecting unit 160' determining whether the coupling factor is currently increasing or decreasing by comparing the latest determined value of the coupling factor to the next latest determined value.

For transmitting the feedback information an internal signal transmitter 113 and an external signal receiver 159 in or connected to the internal charger 107 and the external charger 151, respectively, may be implemented as separate units using suitable signal transfer means, such as using radio waves, IR (Infrared) or ultrasonic signals. Alternatively, the feedback information may be conveyed in a reverse direction relative to the energy transfer, basically using the same transmission method as in the transfer of energy, such as by varying or modulating some electric characteristic of the internal coil 109, e.g. switching it on and off in predetermined patterns, as will be described below. In this case special control and detecting units included in the respective chargers are used. Such units can generally be represented by the shown internal signal transmitter 113 and the external signal receiver 159. Signal transmitting/modulating means and signal receiving/demodulating/detecting means such as the internal signal transmitter and the external signal receiver can be used in the embodiments described herein, where they are required, even if they are indicated the respective drawings.

As a supplement or an alternative to the display 157 the external charger 151 can as above be provided with a unit 156 providing an audible signal, the characteristics of which is changed according to the determined coupling between the external charger and the internal charger 107 such as the determined value of the coupling factor. Thus, the audio unit can emit a sound signal having a low strength or a low pitch when the determined value of the coupling is small and having a higher strength or a high pitch, respectively, when the determined value of the coupling obtains a higher value, the strength or pitch being set according to the determined value. Also, the sound can be emitted as pulses, the repetition frequency of which is changed depending on the value of the coupling.

In an embodiment a switch 115 is provided in the internal power supply 104 for switching on and off the connection between all the other components of the implanted medical device 101 and the first coil 109 arranged for receiving energy from the external charger 151, the first coil thereby constituting an open loop in which an electric current cannot flow, this actually stopping the transfer of energy to the internal charger 107. The internal charger 107 can further provided with a transmission control device 116 connected to the switch 115 setting it on and off according to predetermined patterns, the patterns representing information related to the charging received by the internal charger. This switching on and off can be sensed by the external charger 151 as an impedance variation or impedance modulation of the second coil 153 such as by an impedance sensing unit 162 that can detect the information conveyed in the variations of the impedance. Alternatively, a separate transmitter and a separate receiver can be arranged in the internal charger and the external charger, for transmitting the information related to the charging.

In another embodiment a receiving or sensing unit 163 is provided in the external power supply 150 such as in the external charger 151 for receiving or sensing feedback information that is passively transmitted from the first coil 109, this embodiment not requiring a special control unit in the internal charger 109. Such passively generated feedback information can be obtained as the response induced in the internal, first coil when influenced by a power pulse or burst generated by the external power supply. Such a power pulse or power burst can basically include that a single electric current pulse is applied to the external coil 153 or a train of such pulses or that an electric alternating current is applied to the external coil for a short time period, such as a time period corresponding to half the or the whole period of the alternating current or to a few periods, e.g. two or three such periods. The receiving or sensing unit 163 is then arranged to detect e.g. the magnetic or electromagnetic field generated by the internal charger 107 as a response to the power burst or pulse. By determining the strength of the detected magnetic or electromagnetic field the external charger 151 can determine whether the position becomes better or worse when a user moves the external power supply over the skin of a patient having an implanted medical device 101 including or connected to an internal charger 107. An increase in the response magnetic or electromagnetic field indicates a better energy supply position.

For example, if the power pulse or burst includes only a single pulse such as a rectangular pulse, a voltage is induced in the first coil during the first, leading edge of the pulse. This voltage drives an electric current through the first coil, producing a secondary magnetic field which can be sensed by the receiving or sensing unit 163. If the power pulse or pulse includes a sinusoidal electric current, the first coil will produce a sinusoid ally varying magnetic field that can be sensed by the receiving or sensing unit.

In an initial calibration stage the power pulses or bursts can be transmitted with such characteristics as to increase the response generated by the first coil 109 from a first low level until the resulting magnetic or electromagnetic field can be sensed by the receiving or sensing unit 163. For a rectangular pulse this can include that the leading and/or trailing edges of the pulse are made more steep or that the pulse height is increased, this producing a stronger magnetic field and a magnetic field existing for a longer time period, respectively.

The generation of the power pulse or power burst can be controlled by a control unit 165 in the external charger 151. Such a control unit can control the various functions of the external charger and be provided also in other embodiments described herein whenever necessary or suitable, also in cases where such a control unit is not shown in the respective drawing.

The external power supply 150 may also comprise an analyzing unit similar to the analyzing unit 160 described above but in this case arranged to analyze the passively generated feedback information from the internal charger 107 such as a value of the strength of the detected magnetic or electromagnetic field and to generate a signal representing this information that can be displayed or indicated such as on the display 155 and/or using an audible signal. From the displayed or received information the user can optimize the placement of the external power supply 150 and in particular of the external charger 151 in relation to the internal charger 107 to optimize the transfer of energy to the internal power supply 104.

Furthermore, in order to initiate a procedure for finding an optimal position for charging the internal charger, the external charger 151 can be arranged to perform a calibration procedure involving a sequence of calibration steps as commanded by the control unit 165, as will be described in more detail below. For example, in order to generate a feedback signal from the internal charger 107, the external charger can be arranged or commanded to slowly, e.g. in predetermined steps, increase the level of transmitted energy or power, i.e. the level of the intensity of the current provided to the second coil 153, until a feedback signal is received from the internal charger 104. After a response has been detected and received from the internal charger, the user can start moving the external charger for finding the optimal charging position based on the feedback information from the internal charger.

In the embodiment of FIG. 3b the evaluation of the coupling is made in the internal charger 107 such as in an analysis unit 117. It can receive information about the received energy or power directly from other components of the internal charger and it can also receive information about the transmitted energy such from a receiver 114 receiving such information from a transmitter 164 in the external charger 151. The analysis unit can e.g. calculate a coupling factor and may also detect whether there is currently an increase or a decrease of the coupling factor. Information about the coupling, coupling factor and/or whether the coupling is increasing or decreasing can be sent to the external charger 151 using the transmitter 113 and receiver 159. The information received by the external charger can as above be used for generating a signal, such as an appropriate light signal or a sound signal.

An internal receiver and an external transmitter for receiving and sending control signals or information signals, such as the units 114 and 164 illustrated in FIG. 3b, can be arranged in the internal charger 107 and the external charger 164 also in other embodiments described herein, whenever necessary or suitable, also when symbols of such devices are not shown in the respective drawing.

FIG. 4a is a schematic, partly sectional view of an implanted medical device 101 and an external power supply 150 in which more details can be seen. The implanted medical device comprises or is connected to an internal power supply 104 also implanted in the patient. The internal power supply comprises or is connected to an internal charger 107 arranged to wirelessly receive, through the skin 170 of the patient as described above, energy from the external power supply 150 comprising or connected to an external charger 151. The internal charger is connected to an internal energy source such as an electrochemical cell or a battery 105. The internal energy source supplies energy used for driving active parts, such as mechanical parts, of the implanted medical device 101. The implanted medical device can comprise a control device working in a mechanical or hydraulic way. For example, the implanted medical device can comprise a control device for mechanically or hydraulically adjusting a member 108 located in conjunction with or at a blood vessel 112 or at some other internal organ for controlling the flow of a fluid in the vessel 112 or organ. In FIG. 4a the member 108 is shown as being mechanically or hydraulically adjusted to a generally closed position, thereby shutting off the flow of fluid in the vessel 112.

As can be seen in FIG. 4a, the internal power supply 104 can comprise two portions, a first portion holding the internal charger 107 and a second portion holding the internal energy source 105 and other components. The portions can be interconnected through a relatively narrow tubular part 118 in which the necessary electric lines, not shown, pass. The portions can be implanted at opposite sides of a diaphragm or membrane 119 in the patient's body, this giving the internal power supply a relatively well fixed position not allowing significant movements in the body tissues.

FIG. 4b is a fragmentary sectional view of the control device of the medical device 101. FIG. 4b corresponds to respective portion of FIG. 4a but shows the member 108 mechanically or hydraulically adjusted to a generally open position to allow free flow of the fluid in the vessel 112.

FIG. 5 is another fragmentary, partly sectional view of the internal power supply 104 and the external power supply 150 further illustrating the operation of the charging system as described herein. Hence, in order to find an optimal position of the external charger 151 comprised in or connected to the external power supply that is arranged to transmit energy to the internal charger 107, the external power supply and in particular the external charger is being moved over the skin 170 of the patient. In response to feedback information from the implanted medical device such as from the internal power supply or the internal charger the optimal position for charging the implanted medical device is searched for and selected. The operation of the charging system is further described below with reference to FIG. 6.

FIG. 6 is a flow chart illustrating steps performed when the charging system as described herein is used to find an optimal position for transmitting energy to the internal charger 104 which in turn is arranged to supply power to other parts of the implanted medical device 101. The steps can be commanded by a control unit in the external power supply such as the control unit 165 shown in FIGS. 3a and 3b. In a first step 601 the external charger 151 is turned on, the external charger is placed at some suitable place on the patient's body and procedure for finding the optimal position is started by e.g. pressing a button, not shown, on the external charger. Next in a step 603 the charger performs a calibration procedure in order to produce a response signal from the internal charger 104 that can be detected by the external charger. In the calibration procedure the level of the power supplied to the external coil 153 is increased, e.g. continuously or stepwise, i.e. the strength of the electromagnetic field generated by the external coil is increased by supplying an electric current having a gradually increasing intensity to the external coil. In the next step 605 the user or operator starts to move the external charger over the skin 170 of the patient. Thereupon, in a step 607, the user receives feedback information from the system allowing the user to move the external charger to a position that is more favorable for transmitting energy to the internal charger 107. Upon finding an optimal position the external charger 151 indicates this fact in a step 609 and the procedure ends in a final step 611.

It may happen that the initial position of the external charger 151 is far away from the internal charger 107. Then, the power supplied to the external coil 153 may be rather high in order to produce a response from the internal charger which of course is not desired since it could cause damages. In that case, it can be tested in the calibration step 603, when the external charger is moved whether now a lower power supplied to the external coil can be used. For example, the power can decreased until no response is obtained or received and then increased by a suitable step to produce a response. Such a procedure can be used at regular repeated times during the movement of the external charger 151 until a sufficiently low power is supplied to the external coil.

After the procedure for searching for an optimal position has been performed, the level of the power supplied to the external, second coil 153 is set to a value suitable for the energy transfer, e.g. as commanded by the control unit 165. It can e.g. be set to the lowest possible value that can achieve a desired charging of the internal energy source. Then, in such a setting operation a value of the electromagnetic coupling, if available, between the second coil 153 and the first coil 109, e.g. as representing by the coupling factor, can be considered, this generally resulting in that a low value of the coupling factor requires a high level of the power supplied to the external coil and that a higher value of the coupling factor requires a lower level.

FIG. 7 is a schematic view of an embodiment of an implanted medical device 101 and the charging and power supply system 100 thereof. The internal charger 107 acting as of an energy receiver comprises an energy-transforming device such as a first coil 109. The energy receiver can preferably be located just beneath or just inside the patient's skin 170. Generally, the implanted energy-transforming device or coil 109 may, as in all embodiments described herein, be placed in the abdomen, thorax, muscle fascia, e.g. in the abdominal wall, subcutaneously, or at any other suitable location in the patient's body. The implanted energy-transforming device or first coil 109 is arranged to wirelessly receive energy E transmitted from an external power supply 150 such as from an external charger 151 comprising a second coil 153 provided in the external power supply 150 when it is placed in the vicinity of the implanted energy-transforming device 109.

As is well known in the art, the energy E that is transferred to the internal charger 107 may generally be transferred by means of any suitable Transcutaneous Energy Transfer (TET) device or system, such as a device or system including a primary coil 153, herein also called second coil, arranged in the external charger 151, and an adjacent secondary coil 109, herein also called first coil, arranged in the implanted internal charger 107 as described above. When an alternating electric current flows in the primary coil, an alternating voltage is induced in the secondary coil which can be used to drive an electric current through the second coil that can be used to power energy consuming components 101' of the implanted medical device 101. The electric current flowing in the secondary coil represents received energy that e.g. can be stored in an implanted energy source, such as a rechargeable electrochemical cell or battery 105 or a capacitor. However, at least some aspects of the methods, systems and devices described herein are generally not limited to any particular method of transferring energy or power and to TET devices or energy sources of any particular kind, and in such cases wireless energy transfer of any suitable kind may be used.

The amount of energy received by the implanted, internal charger 107, that can be called an internal energy receiver, may be compared to the energy used by the other implanted components of the system or apparatus. The term "energy used" is then understood to include also energy stored by implanted components of the apparatus but of course not the energy stored in the energy source such as the battery 105 included in or connected to the internal charger 107. A control device, i.e. basically the control system of the energy transfer system, includes an external control unit 165 that controls the external energy source 153 based on the determined energy balance to regulate the amount of transferred energy. In order to transfer the correct amount of energy, the energy balance and the required amount of energy is determined by a determination device including an implanted internal control unit 120 connected between a switch 115 and a main portion of the implanted medical device 101. The internal control unit 120 may thus be arranged to receive various measurements obtained by suitable sensors or the like, not shown, measuring certain characteristics of the implanted medical device 101, somehow reflecting the required amount of energy needed for proper operation of the components of the implanted medical device 101. Moreover, the current condition of the patient may also be detected by suitable measuring devices or sensors, not shown, to provide parameters reflecting the patient's condition. Hence, such characteristics and/or parameters may be related to the current state of the implanted medical device 101, such as power consumption, operational mode and temperature, as well as the patient's condition reflected by parameters such as body temperature, blood pressure, heart beat rate and breathing. Physical parameters of the patient of other kinds and functional parameters of the device are described elsewhere.

Furthermore, an energy source such as an accumulator 1016 may optionally be connected to the implanted energy-transforming device 1002 via the control unit 1015 for accumulating received energy for later use by the implanted medical device. Alternatively or additionally, characteristics of such an accumulator, also reflecting the required amount of energy, may be measured as well. The accumulator may be a rechargeable electrochemical cell or battery, and the measured characteristics may be related to the current state of the battery, any electrical parameter such as energy consumption voltage, temperature, etc. In order to provide sufficient voltage and electric current to drive the other components of the implanted medical device 101, and also to avoid excessive heating, it is clearly understood that the battery should be charged optimally by receiving a correct amount of energy from the implanted energy-transforming device 109, i.e. not too little and not too much. The accumulator may also be a capacitor having corresponding characteristics.

For example, battery characteristics may be measured on a regular basis to determine the current state of the battery, which then may be stored as state information in a suitable storage means in the internal control unit 1015. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 120 of the determination device is arranged to determine the energy balance and/or the currently required amount of energy, either energy per time unit or accumulated energy, based on measurements made by the above-mentioned sensors or measuring devices of the implantable medical device 101 or of the patient or of an implanted energy source if used, or any combination thereof. The internal control unit 1015 can further be connected to an internal signal transmitter 113, arranged to transmit a control signal S reflecting the determined required amount of energy, to an external signal receiver 159 included or connected to the external charger 151. The amount of energy transmitted from the external energy source 153 may then be regulated in response to the received control signal.

Alternatively, the determination device may include the external charger 151. In this alternative, sensor measurements can be transferred to the external control unit 165 in which the received values resulting from the sensor measurements are evaluated to determine the energy balance and/or the currently required amount of energy, thus integrating the above-described function of the internal control unit 120 in the external charger 151. In this case, the internal control unit 120 can be omitted and the sensor measurements are supplied directly to the internal signal transmitter 113 which sends the measurements to the external signal receiver 159 from which they are forwarded to the external control unit. The external control unit determines the energy balance and the currently required amount of energy based on the sensor measurements and produces a control signal controlling the external energy transmitter 153, setting a required or suitable level of the energy transfer.

Hence, the system of FIG. 7 employs the feedback of information indicating the required energy, which is more efficient than other methods solutions because it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for being directly consumed or for storing the energy in an implanted energy source 105 or the like. The different parameters discussed above would thus be used if relevant and needed and then as a tool for determining the actual energy balance. However, such parameters may also be needed per se for any actions taken internally to specifically operate the apparatus.

The internal signal transmitter 113 and the external signal receiver 159 may as above be implemented as separate units using suitable signal transfer means, such as radio, IR (Infrared) or ultrasonic signals. Alternatively, the internal signal transmitter 113 and the external signal receiver 159 may be integrated in the implanted energy-transforming device 109 and the external energy source 153, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy transfer system. Such an integrated information feedback and energy system can comprise an implantable internal energy receiver for wirelessly receiving energy, the energy receiver having an internal first coil 109 and a first electronic circuit connected to the first coil, and an external energy transmitter for wirelessly transmitting energy, the energy transmitter having an external second coil 153 and a second electronic circuit connected to the second coil. The external second coil of the energy transmitter wirelessly transmits energy which is received by the first coil of the energy receiver. The system further comprises a power switch 115 for switching the connection of the internal first coil 109 to the first electronic circuit on and off, such that feedback information related to the charging of the first coil is received by the external energy transmitter as an impedance variation of the external second coil 153, when the power switch switches the connection of the internal first coil to the first electronic circuit on and off. The impedance variation can e.g. be detected by determining the intensity or amplitude of the electric current through the second coil. The second coil is generally the load in an electric circuit, not shown, that includes a main power supply e.g. connected to "mains" or the public electric distribution network, and the electric current flowing therethrough can be sensed by the main power supply.

The power switch 115 can be controlled to be closed or open according to any suitable pattern, such as for example periodically, e.g. the times when the power switch is closed can occur in a regularly repeated pattern and the times when the power switch is closed can occur in a regularly repeated pattern, the patterns having the same repetition frequency. In an alternative the closing and opening of the power switch occur at random times in order not to interfere with other electronic components.

The impedance variation is generally detected or received as a variation between two levels, a maximum level and a minimum level. The variation, i.e. the distance between the two extreme levels, then represents or indicates the electromagnetic coupling between the second coil 153 and the first coil 109. When the external power supply/external charger is being moved in relation to the internal power supply/internal charger, the moving of the external power supply results in a variation of the distance between the two levels depending on the position of said external power supply in relation to the internal power supply. The feedback information such as the impedance variation or some quantity derived therefrom can as described above be used to generate a signal and/or indications to a user. Such indications can then include that it is indicated whether the value of the variation, during the moving of the external power supply, is increasing or decreasing, an increasing value indicating a higher or better electromagnetic coupling or a lower or worse electromagnetic coupling.

In the same way as described above, the external power supply can in an initial stage calibrate the system by increasing the amount of transferred energy to the internal power supply until a response of said switching on and off variation is detected by the external supply, i.e. basically until an impedance variation different from zero, or generally above a suitable positive threshold value, is detected.

The switch 153 can either be separate and controlled by the internal control unit 120 or be integrated in the internal control unit. It should be understood that the switch 153 can be implemented by any type of suitable device such as a transistor, MCU, MCPU, ASIC FPGA or a DA converter or any other electronic component or circuit that may switch the power on and off.

The energy supply arrangement illustrated in FIG. 7 may in one embodiment be operated in the following manner. The energy balance is first determined by the internal control unit 120 of the determination device. A control signal reflecting the required amount of energy is also created by the internal control unit, and the control signal is transmitted from the internal signal transmitter 113 to the external signal receiver 159. Alternatively, the energy balance can instead be determined by the external control unit 165 depending on the implementation, as mentioned above. In the latter case, the control signal may carry measurement results from various sensors. The amount of energy emitted from the external energy source 153 can then be regulated by the external control unit 165, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 153, such as voltage, current, amplitude, wave frequency and pulse characteristics.

The system as described herein above may also be used to obtain information about the coupling factors between the coils 109, 153 in a TET system even to calibrate the system both to find an optimal place for the external coil in relation to the internal coil and to optimize energy transfer. In this case the amount of energy transferred is compared to the amount of energy received. For example, if the external coil is being moved the coupling factor may vary and correctly performed movements could result in the fact that the optimal place of the external coil for energy transfer is found. Preferably, the control unit 165 for external coil 153 is arranged to calibrate the amount of transferred energy to achieve the feedback information in the determination device, before the coupling factor is maximized.

This coupling factor information may also be used as a feedback during energy transfer. In such a case, the energy transfer system as described herein comprises an implantable internal energy receiver for wirelessly receiving energy, the energy receiver having an internal first coil 109 and a first electronic circuit connected to the first coil, and an external energy transmitter for wirelessly transmitting energy, the energy transmitter having an external second coil 153 and a second electronic circuit connected to the second coil. The external second coil of the energy transmitter wirelessly transmits energy which is received by the first coil of the energy receiver. The system further comprises a feedback device for communicating a value of the amount of energy received in the first coil 109 as feedback information, wherein the second electronic circuit includes a determination device for receiving the feedback information and for comparing the amount of transferred energy by the second coil 153 to the feedback information related to the amount of energy received in the first coil in order to obtain the coupling factor between the second coil and the first coil. The energy transmitter may regulate the transmitted energy in response to the obtained value of the coupling factor.

FIG. 8 is a block diagram illustrating various embodiments related to the ways in which received energy can be supplied to and used by the implantable medical device 101. Similar to the example of FIG. 7, an internal energy receiver 109 wirelessly receives energy E from an external energy source 153 which is controlled by a transmission control unit 165. The internal energy receiver 109 may comprise or be connected to a constant voltage circuit, indicated as a dashed box "Constant V" in the figure, for supplying energy at constant voltage to the energy consuming parts 101' of the implantable medical device 101. The internal energy receiver 109 may further comprise a constant current circuit, indicated as a dashed box "Constant I" in the figure, for supplying energy at a constant current intensity to the implantable medical device 101.

The implantable medical device 101 can comprise an energy consuming part or component 101', for example a motor, a pump, a restriction device, or any other medical appliance that requires electric energy for its operation. The implantable medical device 101 may further comprise an energy storage device 105 for storing energy supplied from the internal energy receiver 109. Thus, the supplied energy may be directly consumed by the energy consuming part 101', or stored in the energy storage device 105, or the supplied energy may be partly directly consumed and partly stored. The implantable medical device 101 may further comprise an energy stabilizing unit 121 for stabilizing the energy supplied from the internal energy receiver 109. Thus, the energy may be supplied in a fluctuating manner such that it may be necessary to stabilize the energy before consumed or stored.

The energy supplied from the internal energy receiver 109 may further be accumulated and/or stabilized by a separate energy stabilizing unit 122 located outside the internal charger 107, before being consumed and/or stored by the energy consuming part 101' of the implantable medical device 101. Alternatively, the energy stabilizing unit may be integrated in the internal energy receiver 109. In either case, the energy stabilizing unit may comprise a constant voltage circuit and/or a constant current circuit.

Figure 9:
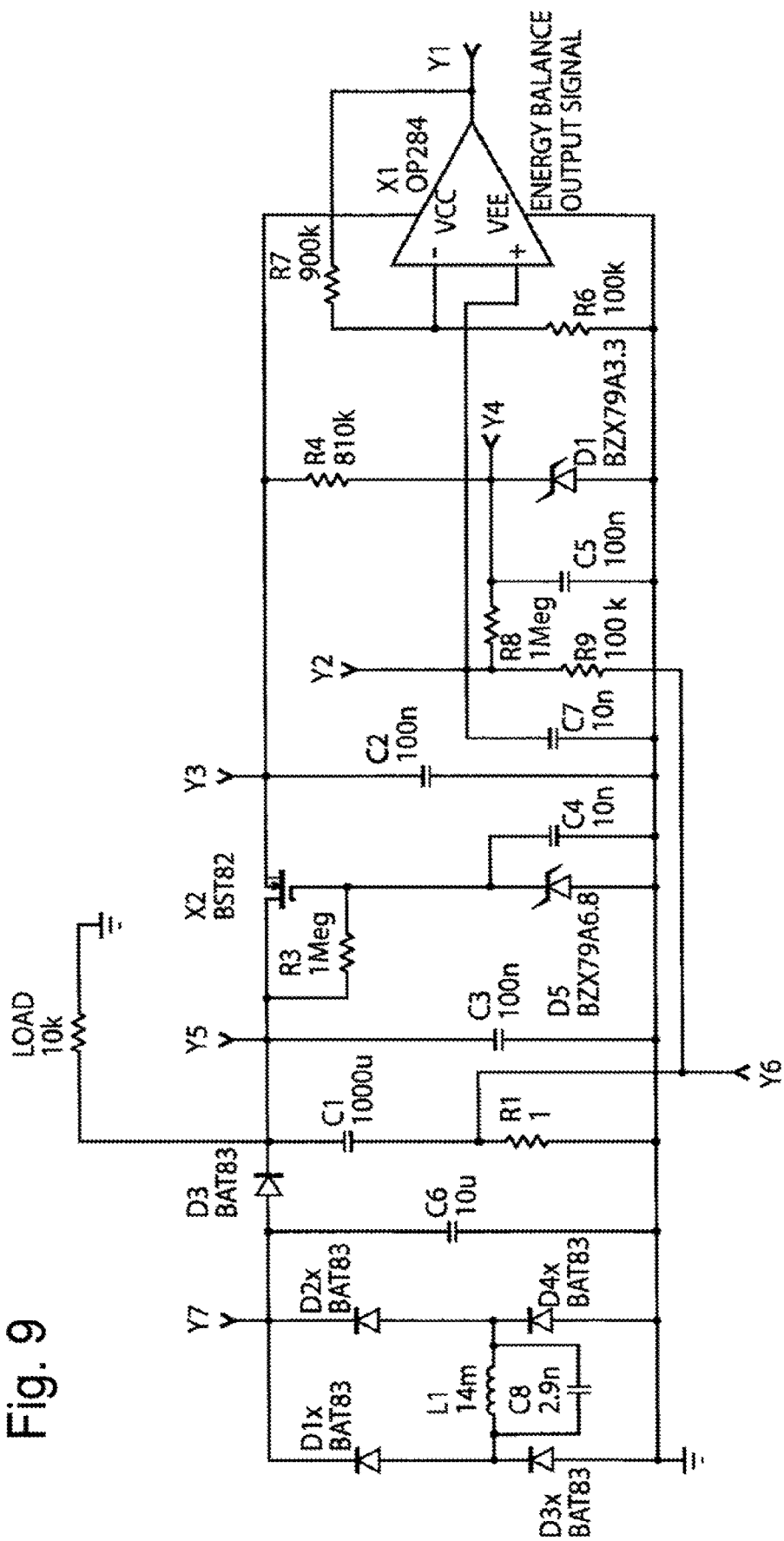
FIG. 9 is a circuit diagram of for a system for transferring energy to implanted components.

FIG. 9 is a circuit diagram of an energy balance measuring circuit of one design of the system for controlling the wireless transmission of energy or of an energy balance control system. The circuit has an output signal that is centered at 2.5 V and is proportionally related to the energy imbalance. The derivative of this signal indicates whether the value is increasing or decreasing and the velocity with which such a change is taking place. If the amount of received energy or power is lower than the energy or power used by implanted components of the device, more energy is transferred and thus charged into the internal energy source. The output signal of the circuit is typically feed to an A/D converter and converted to a digital shape. The digital information can then be sent to the external energy-transmission device allowing it to adjust the level of the transmitted energy. Another possibility is to have a completely analog system that uses comparators comparing the energy balance level to certain maximum and minimum thresholds sending information to the external energy-transmission device if the balance drifts out of the maximum/minimum window.

In particular, FIG. 9 is a circuit diagram of a system for transferring energy to the implanted energy components of the device from outside the patient's body using inductive energy transfer. An inductive energy transfer system typically uses an external transmitting coil and an internal receiving coil. The receiving coil, L1, is included and the transmitting parts of the system are excluded.

The implementation of the general concept of energy balance and the way in which the information is transmitted to the external energy transmitter can of course be made in a multitude of different ways. The circuit diagram of FIG. 9 and the above described method of evaluating and transmitting the information should only be regarded as examples of possible ways in which the control system can be implemented.

Circuit Details

In FIG. 9 the symbols Y1, Y2, Y3 and so on symbolize test points within the circuit. The components in the circuit diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. It can e.g. be observed that the switch simply could mean any electronic circuit or component.

The embodiments described above are related to a method and a system for controlling wireless transmission of energy to implanted energy consuming components of an electrically powered implantable medical device.

A method is thus provided for controlling wireless transmission of energy supplied to implanted energy consuming components of a device as described above. The energy E is wirelessly transmitted from an external energy source located outside the patient and is received by an internal energy receiver located inside the patient, the internal energy receiver being connected to the implanted energy consuming components of the device for directly or indirectly supplying received energy thereto. An energy balance is determined between the energy received by the internal energy receiver and the energy used for the device. The wireless transmission of energy E from the external energy source is then controlled based on the determined energy balance.

The energy that is wirelessly transmitted may e.g. be transmitted inductively from a primary coil in the external energy source to a secondary coil in the internal energy receiver. A change in the energy balance may be detected to control the wireless transmission of energy based on the detected energy balance change. A difference may also be detected between energy received by the internal energy receiver and energy used for the medical device, to control the wireless transmission of energy based on the detected energy difference.

When controlling the energy transmission, the amount of wirelessly transmitted energy may be decreased if the detected energy balance change implies that the energy balance is increasing, or vice versa. The decrease/increase of energy transmission may further correspond to a detected change rate.

The amount of wirelessly transmitted energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or electric current related to the energy balance.

The wireless transmission of energy from the external energy source may be controlled by applying, to the external energy source, electrical pulses from a first electric circuit to wirelessly transmit the energy, the electrical pulses having leading and trailing edges, varying the lengths of first time intervals between successive leading and trailing edges of the electrical pulses and/or the lengths of second time intervals between successive trailing and leading edges of the electrical pulses, and wirelessly transmitting energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied as a group of pulses, wherein when applying the train of pulses, the train having a first electrical pulse at the start of the pulse train and having a second electrical pulse at the end of the pulse train, two or more pulse trains may be supplied sequentially or successively, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising a device as described above is thus also provided for controlling wireless transmission of energy supplied to implanted energy consuming components of the device. In its broadest sense, the system comprises a control device for controlling the wireless transmission of energy from an energy-transmission device, and an implantable internal energy receiver for receiving the wirelessly transmitted energy, the internal energy receiver being connected to implantable energy consuming components of the device for directly or indirectly supplying received energy thereto. The system further comprises a determination device arranged to determine an energy balance between the energy received by the internal energy receiver and the energy used for the implantable energy consuming components of the device, wherein the control device controls the wireless transmission of energy from the external energy-transmission device, based on the energy balance determined by the determination device.

Further, the system may comprise any of the following:
  A primary coil in the external energy source is arranged to wirelessly transmit the energy inductively to a secondary coil in the internal energy receiver.
  The determination device is arranged to detect a change in the energy balance, and the control device controls the wireless transmission of energy based on the detected energy balance change
  The determination device is arranged to detect a difference between energy received by the internal energy receiver and energy used for the implantable energy consuming components of the device, and the control device controls the wireless transmission of energy based on the detected energy difference.
  The control device controls the external energy-transmission device to decrease the amount of wirelessly transmitted energy if the detected energy balance change implies that the energy balance is increasing, or vice versa, wherein the decrease/increase of energy transmission corresponds to a detected change rate.
  The control device controls the external energy-transmission device to decrease the amount of wirelessly transmitted energy if the detected energy difference implies that the received energy is greater than the used energy, or vice versa, wherein the decrease/increase of energy transmission corresponds to the magnitude of said detected energy difference.
  The energy used for the device is consumed to operate the device, and/or stored in at least one energy storage device of the device.

In the case where electrical and/or physical parameters of the device and/or physical parameters of the patient are determined, the energy-transmission device transmits the energy for consumption and storage according to a transmission rate per time unit which is determined by the determination device based on said parameters. The determination device also determines the total amount of transmitted energy based on said parameters.

When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.

In the case where the derivative of a measured electrical parameter over time is determined that is related to the amount of consumed and/or stored energy, the determination device determines the derivative for a monitored voltage and/or a monitored electric current related to the energy balance.

The energy-transmission device comprises a coil placed externally to the human body, and an electric circuit is provided to power the external coil with electrical pulses to wirelessly transmit the energy. The electrical pulses have leading and trailing edges, and the electric circuit is arranged to vary first time intervals between successive leading and trailing edges and/or second time intervals between successive trailing and leading edges of the electrical pulses to vary the power of the wirelessly transmitted energy. As a result, the energy receiver receiving the wirelessly transmitted energy has a varied power.

The electric circuit is arranged to deliver the electrical pulses to remain unchanged except varying the first and/or second time intervals.

The electric circuit has a time constant and is arranged to vary the first and second time intervals only in the range of the first time constant, so that when the lengths of the first and/or second time intervals are varied, the transmitted power over the coil is varied.

The electric circuit is arranged to deliver the electrical pulses to be varied by only varying the lengths of first time intervals between successive leading and trailing edges of the electrical pulses.

The electric circuit is arranged to supply a train of two or more sequential or successive electrical pulses, said train having a first electrical pulse at the start of the pulse train and having a second electrical pulse at the end of the pulse train, where the lengths of the second time intervals between successive trailing edge of the second electrical pulse in a first pulse train and leading edge of the first electrical pulse of a second pulse train are varied by the first electronic circuit.

The electric circuit is arranged to provide the electrical pulses as pulses having a substantially constant height and/or amplitude and/or intensity and/or voltage and/or electric current intensity and/or frequency.

The electric circuit has a time constant, and is arranged to vary the first and second time intervals only in the range of the first time constant, so that when the lengths of the first and/or second time intervals are varied, the transmitted power over the first coil are varied.

The electric circuit is arranged to provide the electrical pulses varying the lengths of the first and/or the second time intervals only within a range that includes the first time constant or that is located relatively close to the first time constant, compared to the magnitude of the first time constant.

Figure 10:
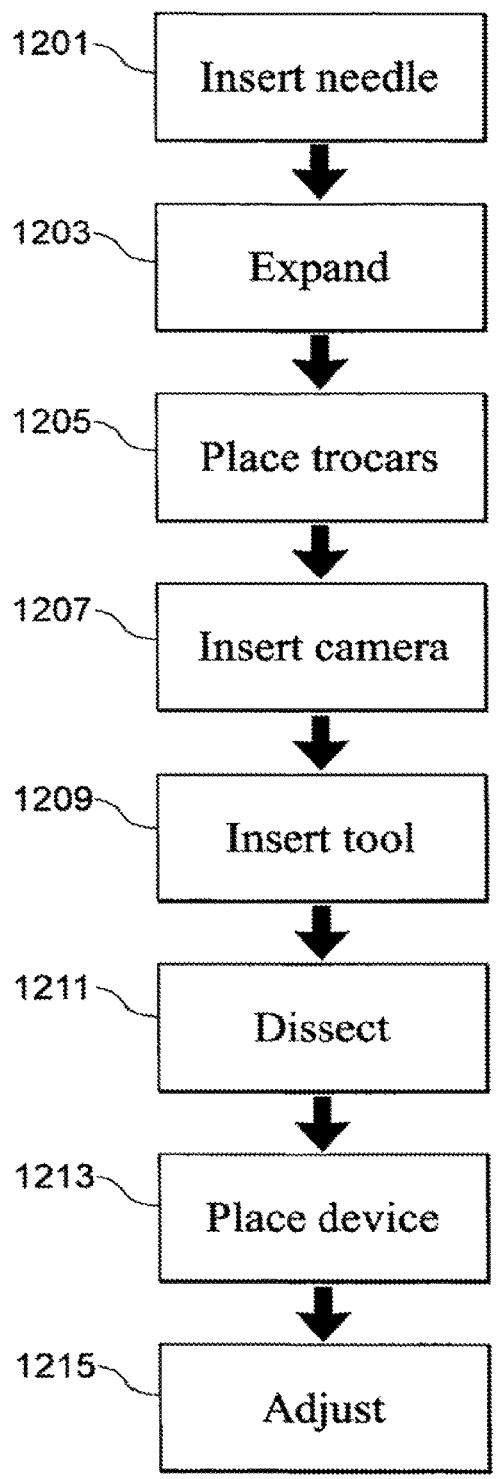
FIGS. 10-13 are flowcharts illustrating different surgical methods.

The internal or implantable devices described herein can be implanted in the body of a patient using a suitable surgical procedure such as that illustrated by the flow chart of FIG. 10. For example, an implantable device can be implanted by inserting a needle or a tubular instrument into the patient's abdominal cavity, step 1201. Next in a step 1203 a part of the patient's body is supplied with gas using the needle or tubular instrument thereby expanding the abdominal cavity. Next in a step 1205 at least two laparoscopic trocars are placed in the cavity. Thereupon in a step 1207 a camera is inserted through one of the laparoscopic trocars into the cavity. Next in a step 1209 at least one dissecting tool is inserted through one of said at least two laparoscopic trocars. An area where the device is to be placed is then dissected in a step 1211. The device is then placed in the area in a step 1213, and the device is adjusted and enabled in a final step 1215.

Figure 11:
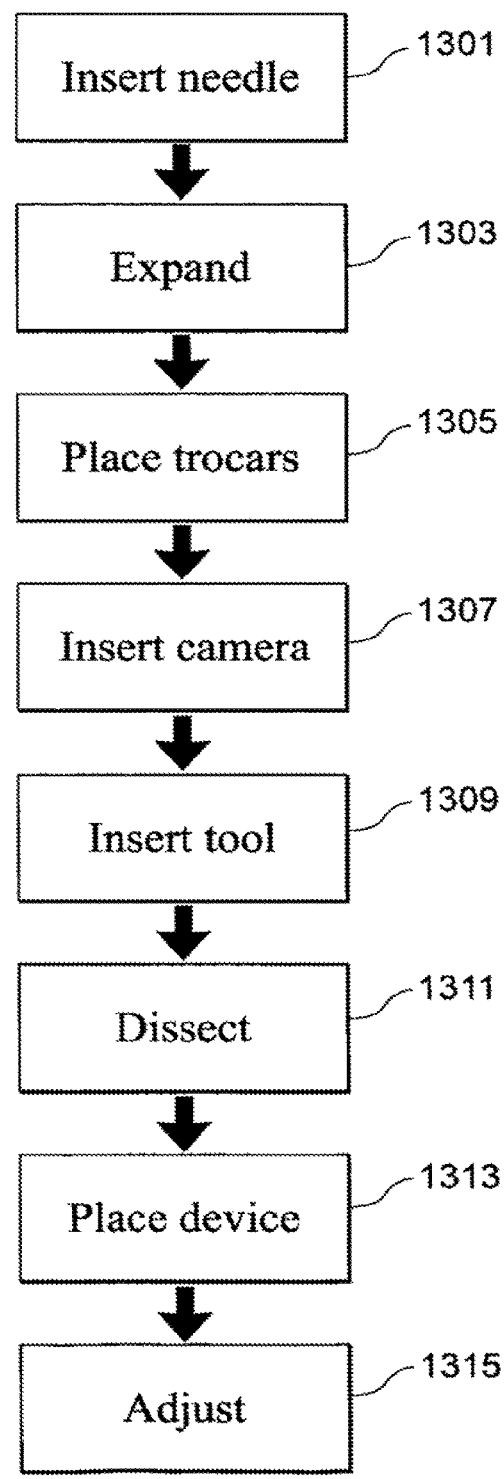

In another embodiment an implantable device can be implanted using a procedure illustrated by the flow chart of FIG. 11. First in a step 1301 a needle or a tubular instrument is inserted into the patient's thoraxial cavity. Next, in a step 1303 a part of the patient's body is supplied with gas using the needle or tubular instrument to fill and thereby expand the thoraxial cavity. Thereupon at least two laparoscopic trocars are placed in the cavity in a step 1305 Thereupon in a step 1307 a camera is inserted through one of the laparoscopic trocars into the cavity. Next in a step 1309 at least one dissecting tool is inserted through one of said at least two laparoscopic trocars. An area is then dissected in a step 1311. The device is then placed in the area in a step 1313, and the device is adjusted and enabled in a final step 1315.

Figure 12:
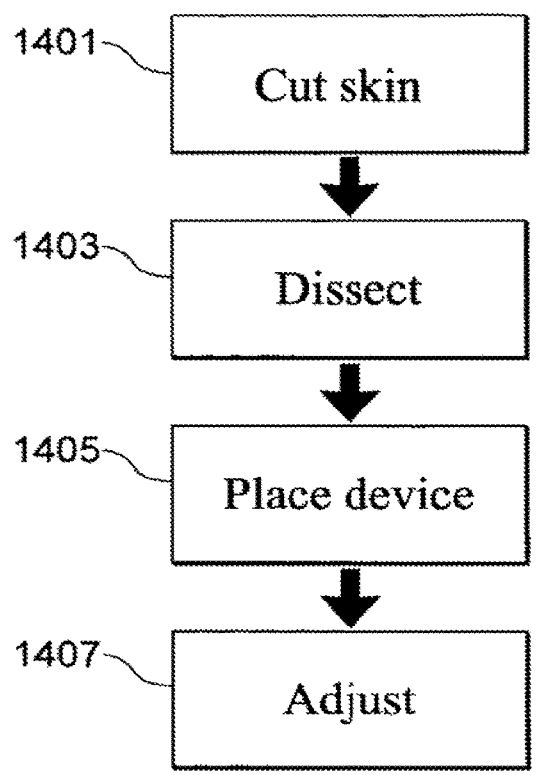

In another embodiment the implantable device can be implanted using a procedure illustrated by the flow chart of FIG. 12. First in a step 1401, the skin in the abdominal or thoraxial wall of the mammal patient is cut. Next, in a step 1403 an area is dissected. Next, the device is placed in the area in a step 1405, and the device is adjusted and enabled in a final step 1407.

Figure 13:
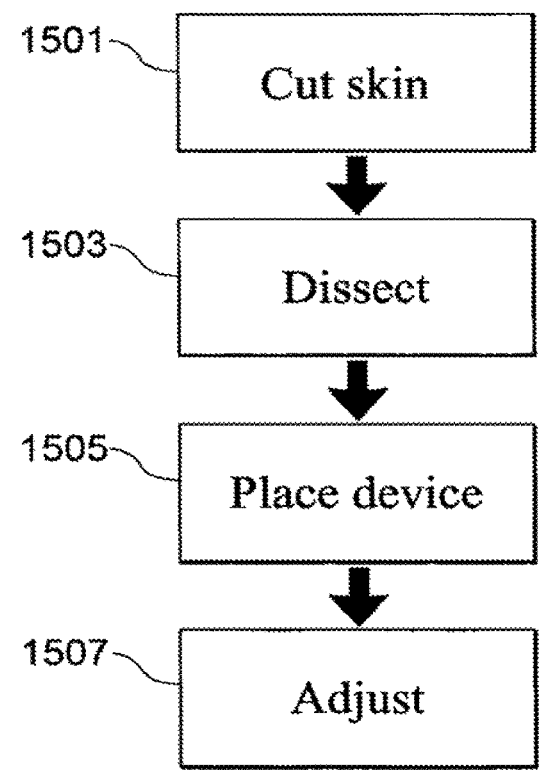

In another embodiment the implantable device can be implanted using a procedure illustrated by the flow chart of FIG. 13. First in a step 1501, the skin of the mammal patient is cut. Next, in a step 1503 an area is dissected. Next, the device is placed in the area in a step 1505, the gas pressure is released and the device is adjusted and enabled in a final step 1507.

It should be observed that the description above illustrate some possible but non-limiting implementation options regarding the ways in which the various shown functional components and elements can be arranged and connected to each other. However, a person skilled in the art will readily appreciate that many variations and modifications can be made within the scope of the present invention.

A use of the method, systems and devices described herein will in many cases provide an efficient transfer, in at least some cases even a more efficient transfer compared to prior art systems and devices, of energy from an external charger to an internal charger providing electric power to an implanted medical device.

While specific embodiments of the invention have been illustrated and described herein, it is realized that numerous other embodiments may be envisaged and that numerous additional advantages, modifications and changes will readily occur to those skilled in the art without departing from the spirit and scope of the invention. Therefore, the invention in its broader aspects is not limited to the specific details, representative devices and illustrated examples shown and described herein. Accordingly, various modifications may be made without departing from the spirit or scope of the general inventive concept as defined by the appended claims and their equivalents. It is therefore to be understood that the appended claims are intended to cover all such modifications and changes as fall within a true spirit and scope of the invention. Numerous other embodiments may be envisaged without departing from the spirit and scope of the invention.

The invention claimed is:

1. A medical device for supplying feedback information when implanted in the body of a patient, the medical device being arranged to monitor or control a physiological condition or defect in the body of the patient and comprising a measuring device for measuring a parameter reflecting the patient's condition, the medical device comprising:
   a radio frequency identification (RFID) device comprising a transmitter arranged to transmit feedback information comprising the parameter reflecting the patient's condition from the implanted medical device, wherein the RFID device comprises a receiver arranged to receive interrogating signals from an external device and, wherein the transmitter, in response thereto, is arranged to transmit feedback information, wherein the feedback information is stored in the identification of the RFID device, wherein the feedback information is transmitted by transmitting the identification of the RFID device.

2. A medical device according to claim 1, wherein the feedback information comprises at least one of the patient's body temperature, blood pressure, heart beat rate and breathing.

3. A medical device according to claim 1, wherein the RFID transmitter is a passive RFID transmitter.

4. A medical device according to claim 1, further comprising a mechanical or hydraulic control device.

5. A medical device according to claim 1, further comprising a control device for mechanically or hydraulically adjusting a member located in conjunction with an internal vessel or organ for controlling the flow of a fluid in the vessel or organ.

6. The medical device according to claim 1 comprising more than one RFID transmitter, wherein RFID transmitters are arranged to respond selectively so that there is a specific interrogation signal for each transmitter.

7. A system for supplying feedback information, the system comprising:
   a medical device arranged to be implanted in the body of a patient, the medical device being arranged to monitor or control a physiological condition or defect in the body of the patient and comprising a measuring device for measuring a parameter reflecting the patient's condition,
   an internal device connected to said implanted medical device, comprising a radio frequency identification (RFID) transmitter arranged to transmit feedback information comprising the parameter reflecting the patient's condition from the implanted medical device, the internal device being arranged to be implanted in the patient's body,
   an external device comprising a RFID receiver arranged to wirelessly receive feedback information from the internal device, wherein the feedback information is stored in the identification of the RFID device, wherein the feedback information is transmitted by transmitting the identification of the RFID device.

8. A system according to claim 7, wherein the feedback information comprises at least one of the patient's body temperature, blood pressure, heart beat rate and breathing.

9. A system according to claim 7, wherein the external device comprises a transceiver for issuing interrogating signals and receiving transmitted RFID signals from the wireless feedback system in response thereto, and wherein the RFID receiver is comprised in the transceiver.

10. A system according to claim 7, wherein the RFID transmitter is a passive RFID transmitter.

11. A system according to claim 7, wherein the external device comprises a display arranged to display and/or indicate the feedback information or information derived therefrom.

12. A system according to claim 11, wherein the display comprises a number of differently colored light sources.

13. A system according to claim 7, wherein the system comprises more than one RFID transmitter or receiver.

14. A system according to claim 7, wherein the system comprises a wireless feedback system arranged to transmit feedback information from the internal device to the external device, wherein the feedback information is based on information from at least one Radio Frequency Identification, RFID, transmitter.

15. A system according to claim 7, wherein the internal device comprises an internal charger for supplying energy to the implanted medical device, and the external device comprises an external charger arranged to wirelessly transmit energy to the internal power supply.

16. A system according to claim 15, wherein the internal charger comprises a first coil and the external charger is arranged to wirelessly transmit energy with an electromagnetic field to supply the internal charger with energy, the external charger comprising a second coil, and wherein the system further comprises
   a wireless passive feedback system adapted to be powered by a wireless signal transmitted by the external charger and arranged to transmit energy-transmission feedback information from the internal charger to the external charger, wherein the energy-transmission feedback information is based on information obtained from at least one radio frequency identification (RFID) transmitter,
   wherein an RFID signature is set in response to a magnitude of the electromagnetic field received as actively measured by a measurement unit in the internal charger, measuring an electric parameter, wherein the measuring unit of the internal charger provides to the at least one RFID transmitter a determined value related to the magnitude of the received electromagnetic field and the at least one RFID transmitter is adapted to set and change its identification according to the determined value related to the magnitude of the received electromagnetic field and to be passively powered by the wireless energy, transmit the changed identification as feedback, and
   wherein the external charger is arranged to regulate the wirelessly transmitted energy based on a relation between; the energy-transmission feedback information being related to an amount of energy received in the first coil, and an amount of wirelessly transmitted energy by the second coil.

17. A system according to claim 16, wherein the feedback information is related to the strength of an electromagnetic field generated by the external charger.

18. The system according to claim 16, wherein the external charger further comprises an indicator arranged to indicate an optimal or closest possible placement of the second coil in relation to the first coil.

19. The system according to claim 15, wherein the external charger further comprises an indicator arranged to indicate an improved or worsened relative position of the external charger or the internal charger, respectively, and the at least one RFID transmitter or a positive or negative change of the distance between the external charger or the internal charger, respectively, and the at least one RFID transmitter.

20. The system according to claim 7, comprising more than one RFID transmitter, wherein RFID transmitters are arranged to respond selectively so that there is a specific interrogation signal for each transmitter.

* * * * *